US011530456B2

(12) United States Patent
Hede et al.

(10) Patent No.: US 11,530,456 B2
(45) Date of Patent: Dec. 20, 2022

(54) DETECTION OF ENDONUCLEASE ACTIVITY

(71) Applicants: AARHUS UNIVERSITET, Aarhus C (DK); THE CHINESE UNIVERSITY OF HONG KONG, Hong Kong (CN)

(72) Inventors: Marianne Smedegaard Hede, Viby J (DK); Birgitta Ruth Knudsen, Viby J (DK); Magnus Stougaard, Højbjerg (DK); Yi-Ping Ho, Hong Kong (CN)

(73) Assignees: Aarhus Universitet, Aarhus C (DK); The Chinese University of Hong Kong, Hong Kong (CN)

( * ) Notice: Subject to any disclaimer, the term of this patent is extended or adjusted under 35 U.S.C. 154(b) by 95 days.

(21) Appl. No.: 17/041,287

(22) PCT Filed: Apr. 4, 2019

(86) PCT No.: PCT/EP2019/058478
§ 371 (c)(1),
(2) Date: Sep. 24, 2020

(87) PCT Pub. No.: WO2019/193083
PCT Pub. Date: Oct. 10, 2019

(65) Prior Publication Data
US 2021/0108251 A1  Apr. 15, 2021

(30) Foreign Application Priority Data

Apr. 4, 2018  (DK) .......................... PA 2018 70196

(51) Int. Cl.
*C12Q 1/689* (2018.01)
*C12Q 1/6851* (2018.01)

(52) U.S. Cl.
CPC .......... *C12Q 1/689* (2013.01); *C12Q 1/6851* (2013.01); *C12Q 2521/319* (2013.01); *C12Q 2521/501* (2013.01); *C12Q 2525/301* (2013.01); *C12Q 2531/125* (2013.01); *C12Q 2533/107* (2013.01)

(58) Field of Classification Search
CPC ...... C12Q 1/682; C12Q 1/689; C12Q 1/6851; C12Q 2521/313; C12Q 2521/319; C12Q 2521/501; C12Q 2525/301; C12Q 2531/125; C12Q 2533/107
See application file for complete search history.

(56) References Cited

U.S. PATENT DOCUMENTS

2007/0009944 A1   1/2007  Bowater et al.
2014/0155284 A1*  6/2014  Koch ................... C12Q 1/6893
                                               435/6.15

FOREIGN PATENT DOCUMENTS

| EP | 2048248 A1 | 4/2009 |
| WO | WO 03/052138 A2 | 6/2003 |
| WO | WO 2012/149936 A2 | 11/2012 |
| WO | WO 2013/029631 A2 | 3/2013 |
| WO | WO 2015/173415 A1 | 11/2015 |

OTHER PUBLICATIONS

Champoux, James J. "DNA Topoisomerases: Structure, Function, and Mechanism" Annu. Rev. Biochem., 2001, pp. 369-413, vol. 70.
Hede, Marianne Smedegaard et al., "Detection of the Malaria causing Plasmodium Parasite in Saliva from Infected Patients using Topoisomerase I Activity as a Biomarker" Scientific Reports, 2018, vol. 8, No. 4122.
Pingoud, A. et al., "Type II restriction endonucleases: structure and mechanism" CMLS, Cell. Mol. Life Sci., 2005, pp. 685-707, vol. 62.
Podgórska, Beata et al., "A rapid and simple method for detection of type II restriction endonucleases in cells of bacteria with high activity of nonspecific nucleases" Acta Biochimica Polonica, Nov. 2012, pp. 669-672, vol. 59, No. 4.
Snounou, Georges et al., "Supercoiling and the mechanism of restriction endonucleases" Eur. J. Biochem, 1984, pp. 275-280, vol. 138.
Tesauro, Cinzia et al., "Specific Detection of Topoisomerase I from the Malaria Causing P. falciparum Parasite using Isothermal Rolling Circle Amplification" 34$^{th}$ Annual International Conference of the IEEE Engineering in Medicine and Biology Society, Aug./Sep. 2012, pp. 2416-2419.
Wang, Jing et al., "Novel DNA sensor system for highly sensitive and quantitative retrovirus detection using virus encoded integrase as a biomarker" Nanoscale, 2017, pp. 440-448, vol. 9.
International Search Report for PCT/EP2019/058478 dated Jun. 12, 2019.

* cited by examiner

*Primary Examiner* — David C Thomas
(74) *Attorney, Agent, or Firm* — Knobbe Martens Olson & Bear LLP

(57) ABSTRACT

The present invention relates to methods for determining endonuclease activity in a sample. In particular, the present invention relates to a method for determining viable pathogenic bacteria in a sample based on patterns of endonuclease activity.

23 Claims, 20 Drawing Sheets
Specification includes a Sequence Listing.

| | EcoRI | XhoI | PstI | SacII | KpnI | BamHI | HpaII | MluI | BsiWI | BsrGI | BstBI |
|---|---|---|---|---|---|---|---|---|---|---|---|
| Sub. EcoRI | ∫ | - | - | - | - | - | - | - | - | - | - |
| Sub. XhoI | - | ∫ | - | - | - | - | - | - | - | - | - |
| Sub. PstI | - | - | ∫ | - | - | - | - | - | - | - | - |
| Sub. SacII | - | - | - | ∫ | - | - | - | - | - | - | - |

Fig. 2

A
SacII
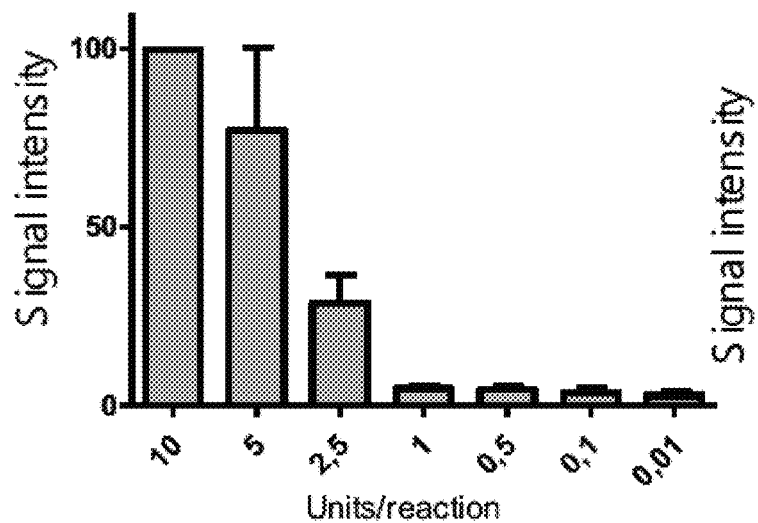
B
XhoI
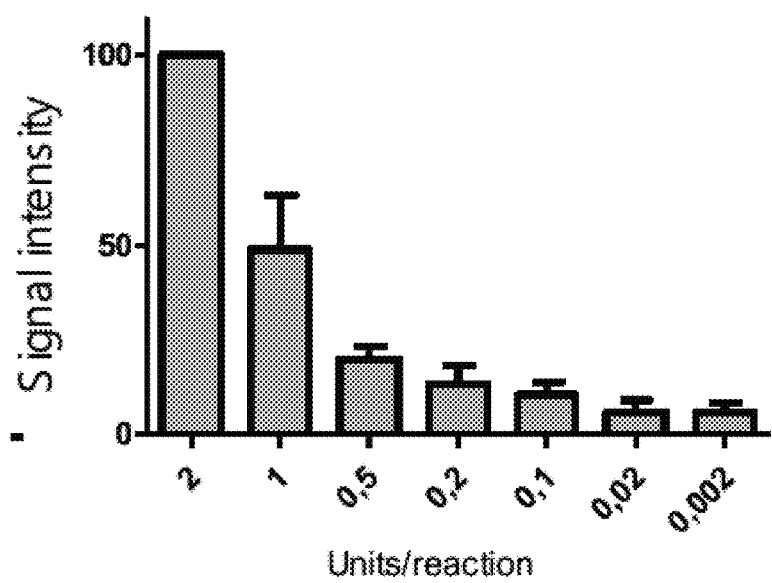
Fig. 3, continues

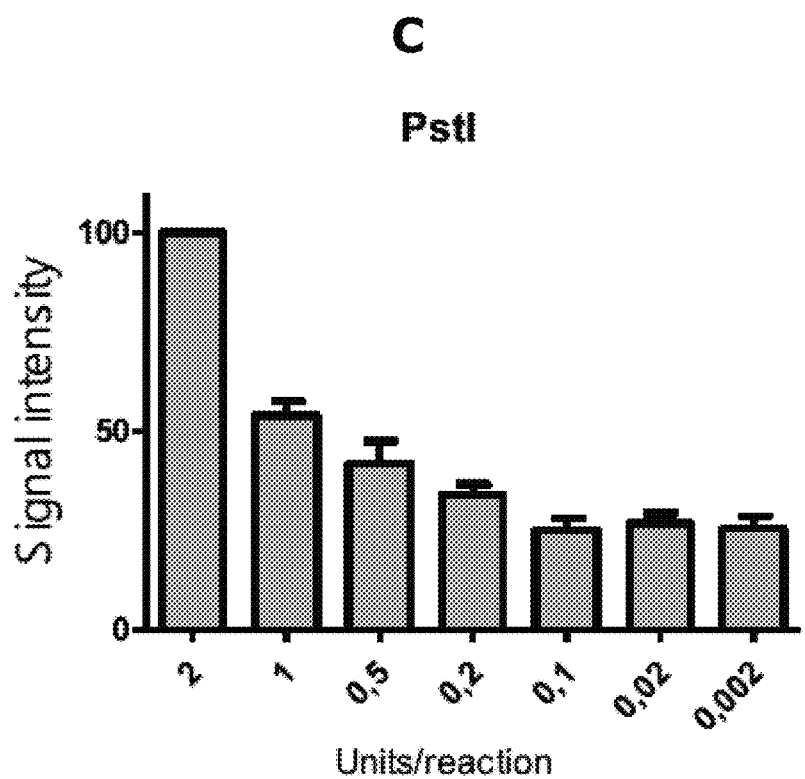
Fig. 3, continued

| Example, name | Proto-type | Recognition site | Cleavage site, prototype | Target organism |
|---|---|---|---|---|
| Lmo1091P | MboI | GATC | ^GATC | Listeria monocytogenes |
| LmoAL4EORF9380P | Lmo911II | TAGRAG | ? | Listeria monocytogenes |
| Lmo1926P | BciVI | GTATCC | GTATCC (6/5) | Listeria monocytogenes |
| Cje47ORF8375P | HaeIII | GGCC | GG^CC | Campylobacter jejuni |
| Cje0410RF8410P | NlaIII | CATG | CATG^ | Campylobacter jejuni |
| Cje690ORF7525P | HphI | GGTGA | GGTGA(8/7) | Campylobacter jejuni |
| PaeD9ORF9925P | PstI | CTGCAG | CTGCA^G | Pseudomonas aeruginosa |
| PaeMH38ORF5188P | XhoI | CTCGAG | C^TCGAG | Pseudomonas aeruginosa |
| PaeAES1RORF2960P | SacII | CCGCGG | CCGC^GG | Pseudomonas aeruginosa |
| SenK61ORFDP | AvaII | GGWCC | G^GWCC | Salmonella enterica |
| Sen1855ORF3705P | PvuII | CAGCTG | CAG^CTG | Salmonella enterica |
| Sen44E09ORF2278P | XmaIII | CGGCCG | C^GGCCG | Salmonella enterica |
| Sau110ORFCP | Fnu4HI | GCNGC | GC^NGC | Staphylococcus aureus |
| SauS100ORF8520P | ScrFI | CCNGG | CC^NGG | Staphylococcus aureus |
| Sau98I | SmlI | CTYRAG | C^TYRAG | Staphylococcus aureus |

Fig. 12

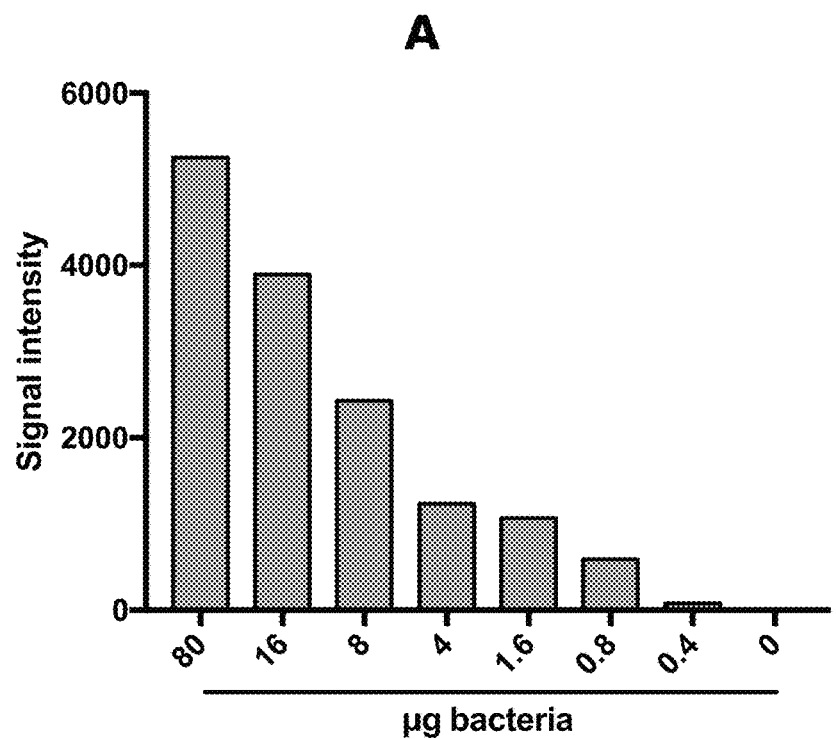
Fig. 17, continues

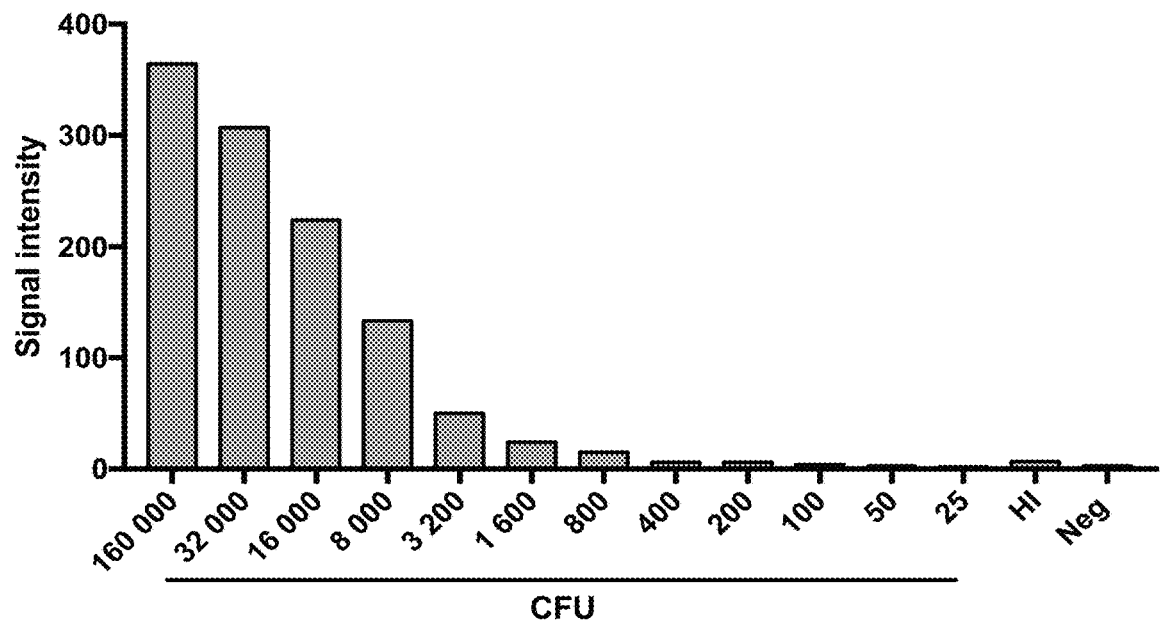
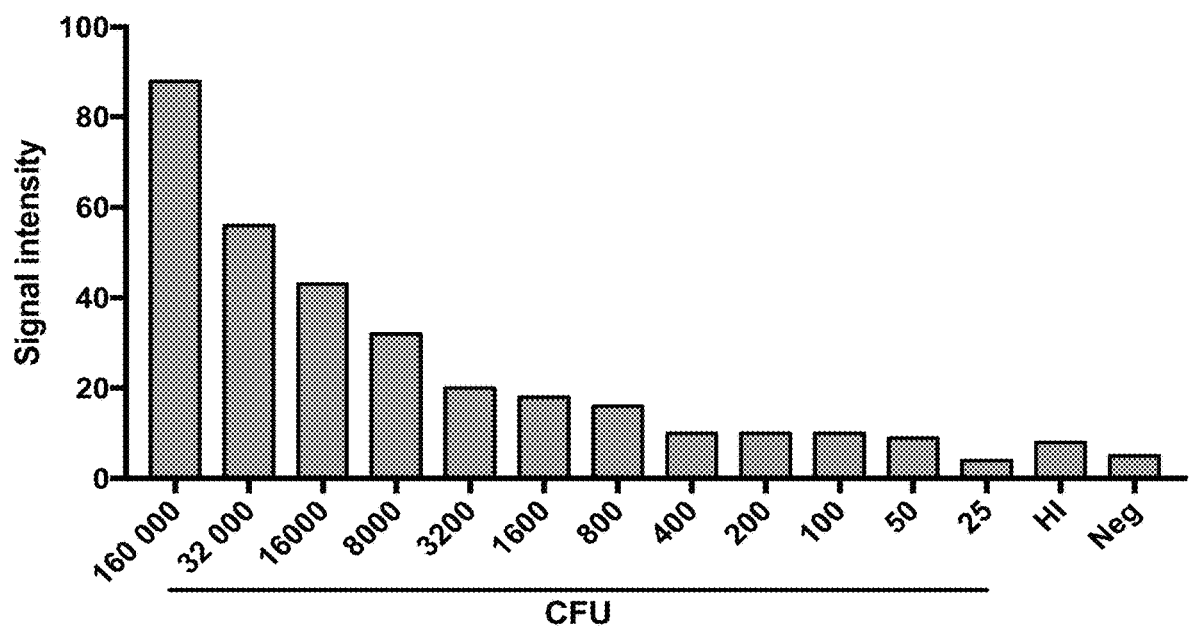
Fig. 17, continued

DETECTION OF ENDONUCLEASE ACTIVITY

CROSS REFERENCE TO RELATED APPLICATIONS

This application is a U.S. National Phase Application of PCT International Application Number PCT/EP2019/058478, filed on Apr. 4, 2019, designating the United States of America and published in the English language, which is an International Application of and claims the benefit of priority to Danish Patent Application No. PA 2018 70196, filed on Apr. 4, 2018. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-PLOUG23-024APC.txt, the date of creation of the ASCII text file is Sep. 24, 2020, and the size of the ASCII text file is 8.09 KB.

TECHNICAL FIELD OF THE INVENTION

The present invention relates to a method for determining endonuclease activity in a sample. In particular, the present invention relates to a method for determining viable bacteria in a sample based on patterns of endonuclease activity.

BACKGROUND OF THE INVENTION

There is a general need for novel fast methods for detection of bacteria in samples. Different methods have been presented, where enzyme activity has been used to determine the presence of microorganisms. For example, Wang J et al. (Nanoscale. 2017 Jan. 7; 9(1):440-8) has presented a novel DNA sensor system for highly sensitive and quantitative retrovirus detection using virus encoded integrase as a biomarker. Also Tesauro C et al (Annual International Conference of the IEEE Engineering in Medicine and Biology Society IEEE Engineering in Medicine and Biology Society Annual Conference. 2012; 2012:2416-9) has presented a method for specific detection of topoisomerase I from the malaria causing *P. falciparum* parasite using isothermal rolling circle amplification. WO2015173415 discloses a method of identifying a microorganism that expresses a nucleic acid-modifying enzyme in a sample.

WO2012149936 discloses methods for the identification of microorganisms or infectious disorders, especially by using substrates for type 1 topoisomerases. WO2013029631 discloses microfluidic-implemented methods of detecting an enzyme, in particular a DNA-modifying enzyme. The enzyme is detected by providing a nucleic acid substrate, which is specifically targeted by that enzyme.

However, novel methods for determining other types of enzyme activities are needed. Hence, an improved method for identifying microorganisms based on enzyme activities would be advantageous, and in particular a more efficient and/or reliable method for differentiating viable microorganisms from non-viable would be advantageous.

SUMMARY OF THE INVENTION

The present invention relates to a method of detection of bacterially expressed restriction enzyme endonuclease (restriction enzyme (RE)) activities e.g. for detection of viable/living bacteria in a highly sensitive and specific manner. The assay is characterized by high endonuclease abundance (>1000 per cell), combined with each endonuclease generating many products (several hundred conversions per enzyme molecule per hour). The generated products are detected after signal amplification e.g. by simple isothermal DNA techniques or PCR. Due to these characteristics, the technology aspire to have the sensitivity of at least the currently used qPCR tests while at the same time being easy enough to allow "on-site" monitoring. Hence, the present method will be attractive for e.g. first line and fast surveillance of production lines.

As mentioned, the method utilizes a pathogen's own endonuclease activity as a biomarker for detection. Endonuclease are expressed by bacteria as a part of the bacterial defense against bacteriophages. The bacteria protects its own DNA by subjecting it to modifications (typically methylation) that prevents cleavage of "self" DNA by the endonucleases that it express. The expressed endonucleases thus exclusively digest foreign DNA (bacteriophage DNA).

A completely novel and highly flexible DNA substrate design for detection of RE activity has been developed. The substrate design allows easy modification for detection of any type II restriction endonuclease of interest. Restriction endonucleases cleave DNA at a specific DNA sequence, which varies from enzyme to enzyme. In one preferred embodiment, the method of the invention is based on a set of two DNA substrates, which carries the cleavage site for a specific endonuclease (FIG. 1A and FIG. 11). Each of the two substrates carries one of two elements necessary for detection by a polymerase assisted amplification. One substrate carries the primer binding site needed for priming the RCA reaction. The other substrate carries a detection sequence needed for detection of the RCA product. "Ligation blocks" at the 3' and 5' end of the DNA substrates (e.g. by amines) ensure that in the uncleaved state, the substrates cannot fuse and create a detectable DNA product carrying both needed elements. In the presence of the target enzyme, the substrates are cleaved, which removes the amines and allows fusion of the two elements by a DNA ligase. The detectable DNA product is a covalently closed DNA circle, which can be amplified and detected at the single molecule level or in bulk. Embodiments of the method are also schematically outlined in FIGS. 1A and 1*n* FIGS. 8-11.

The method of the present invention has been developed and tested using e.g. *E. coli* and *Mycobacteria smegmatis* as model organisms (see example section). The system may be adapted to detection of a broad range of different bacteria simply by utilizing the fact that bacteria species or strains of bacteria have been demonstrated to express unique sets of endonucleases each of which target a highly specific DNA sequence. To exploit the technology for specific detection of bacteria of interest a bioinformatic approach has been used to identify sets of restriction endonuclease activities expressed by bacteria of interest (example 8). In the example section, it is further demonstrated that it is feasible to quantitatively detect model bacteria based on enzyme expression pattern and distingue between living and dead bacteria.

Thus, an object of the present invention relates to the provision of a method for determining endonuclease activity in a sample. In particular, it is an object of the present invention to provide a method that solves the above-mentioned problems of the prior art with fast determination of viable bacteria in a sample.

Thus, one aspect of the invention relates to a method for screening for endonuclease activity in a sample, the method comprising
- a) providing a sample (S) to be analyzed;
- b) adding to the sample (S) at least one first oligonucleotide (1), to obtain a first reaction composition, the at least one first oligonucleotide (1) comprising a hairpin structure, wherein the stem of said hairpin structure comprises a first cleavage site (2) for a first endonuclease;
- c) adding a ligase to the first reaction composition obtained in b), to circularize at least the first oligonucleotide (1) if a endonuclease present in the sample (S) have cleaved the cleavage site (2) in the first oligonucleotide (1), wherein the produced circularized molecules (3) comprise part of stem-loop structures of the first oligonucleotide (1) after endonuclease cleavage;
- d) performing an amplification reaction using the at least first circularized oligonucleotides (3) as template, such as by RCA, PCR or LAMP; and
- e) detecting the amplified product from step d), thereby determining endonuclease activity in said sample.

Another aspect of the present invention relates to a kit comprising
- A first container comprising a composition comprising at least one first oligonucleotides (1); the first oligonucleotide (1) comprising a hairpin structure, wherein the stem of said hairpin structure comprises a cleavage site (3) for a first endonuclease;
- optionally, a second container comprising a composition comprising at least a second oligonucleotides (4), the second oligonucleotide (4) comprising a hairpin structure, wherein the stem of said hairpin structure comprises a restriction site (3) for the first endonuclease;
- optionally, instruction for using said kit to determine the presence of nuclease activity in a sample;
- optionally, a third container comprising a ligase;
- optionally, a fourth container comprising a polymerase;
- optionally, a fifth container comprising one or more primers; and
- optionally, a sixth container comprising one or more detection oligonucleotides (9).

Yet another aspect of the present invention is to provide uses of the method of the invention or the kit according to the invention to screen for the presence of viable (pathogenic) bacteria in a sample.

BRIEF DESCRIPTION OF THE FIGURES

FIG. 2 shows that detection of individual target enzymes is specific. The substrate designed to react with EcoRI (Sub. EcoRI) is specific for EcoRI among the enzymes tested. Likewise, the substrates for PstI, XhoI, and SacII are specific for their respective target enzymes. A tick mark indicates positive signal whereas a minus indicates no signal.

FIG. 3 shows quantitative detection of Pseudomonas relevant target enzymes in purified form. The quantitative nature of the method of the invention was demonstrated using three different target enzymes, SacII, XhoI and PstI.

Design of a microfluidic chip. The single inlet and outlet are separated by a serpentine channel.

FIG. 8

Outline of an amplification process using a microfluidic chip.

Figure 9:
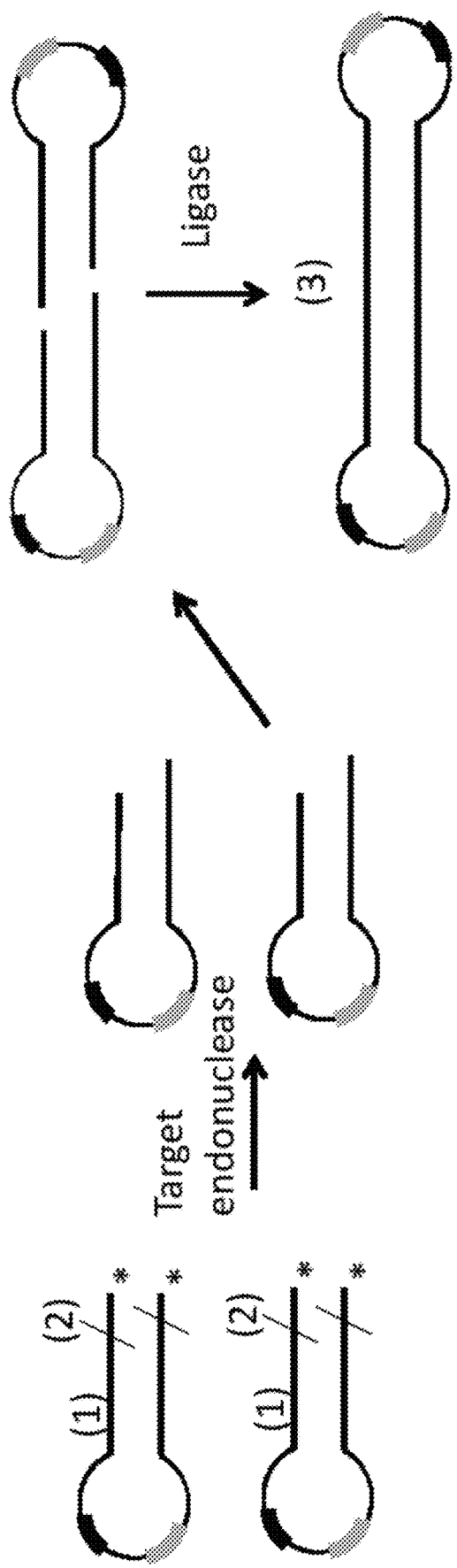

FIG. 9 illustrates one embodiment of the invention, where the circularization step is performed using one hairpin oligonucleotide (1). Target sites for the specific endonuclease of interest is marked by (2). The two identical oligonucleotides (denoted (1)) are cleaved by the target endonuclease recognizing the target site (2). This removes a ligation block (asterisks) thereby allowing ligation and formation of a circular product (3). The circularized product can subsequently be amplified by e.g. RCA. Thick grey element illustrate binding site for a detection oligonucleotide after amplification by RCA and the black elements represent a primer binding site for RCA or vice versa.

Figure 10:
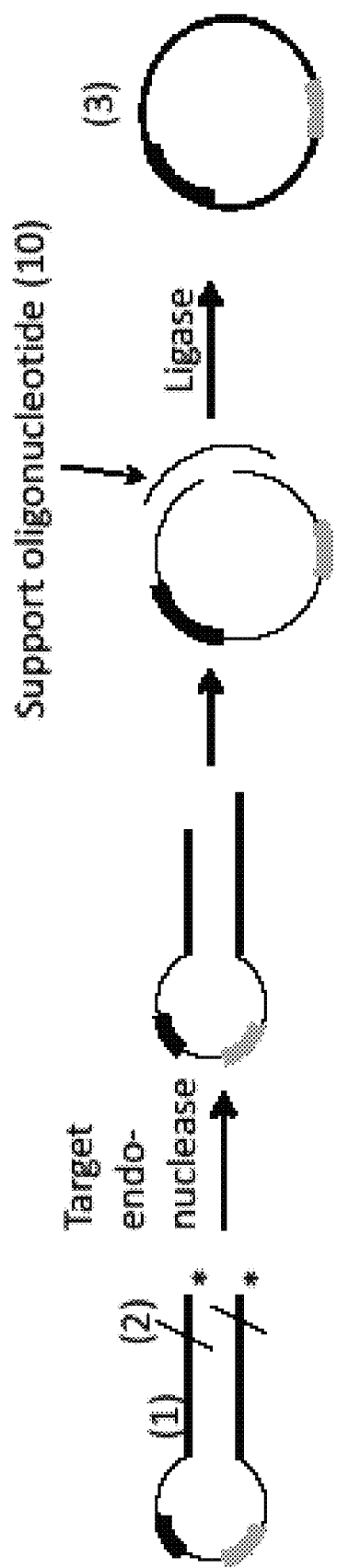

FIG. 10 illustrates one embodiment of the invention, where the circularization step is performed using one hairpin oligonucleotide (1) and one support oligonucleotide (10) to support hybridization and ligation. Target sites for the specific endonuclease of interest is marked by (2). The oligonucleotide (1) is cleaved by the target endonuclease recognizing the target site (2). This removes ligation blocks (asterisks) thereby allowing ligation and formation of a circular product (3). Ligation is dependent on a support oligonucleotide (10) rendering the unligated circle partly double-stranded which is necessary for ligation. The circularized product can subsequently be amplified by e.g. RCA. Thick grey element illustrate binding site for a detection oligonucleotide after amplification by RCA and the black elements represent a primer binding site for RCA or vice versa.

Figure 11:
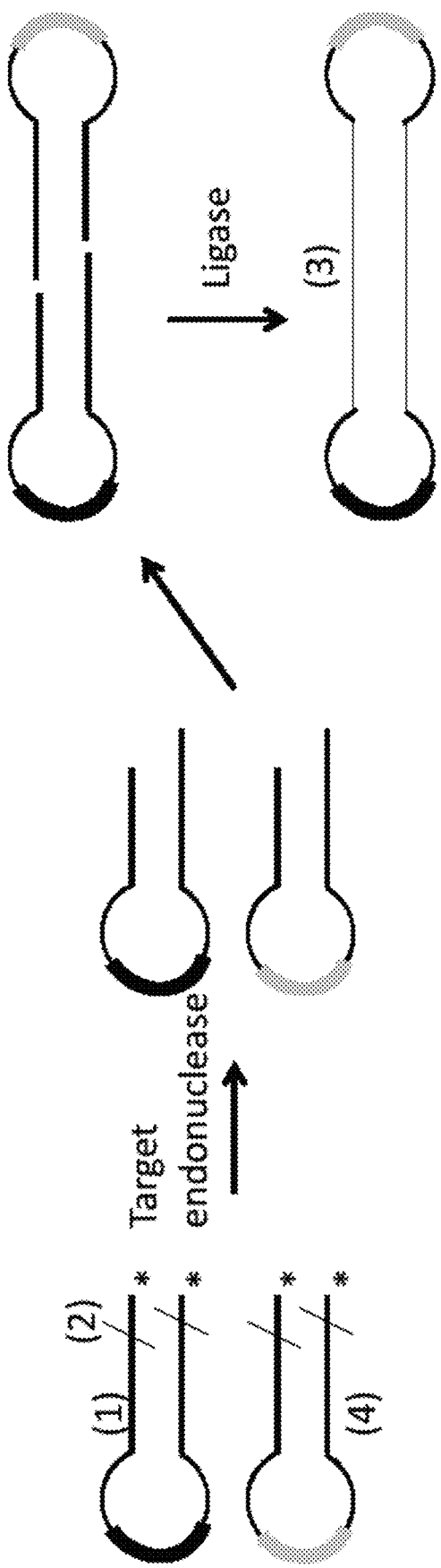

FIG. 11 illustrates one preferred embodiment of the invention, where the circularization step is performed using two hairpin oligonucleotides (1) and (4) Target sites for specific endonuclease of interest is marked by (2). The two oligonucleotides (denoted (1) and (4)) are cleaved by the target endonuclease(s) recognizing the target site (2) present in both oligonucleotides. This removes the ligation blocks (asterisks) allowing ligation and formation of a circular product (3). The circularized product can subsequently be amplified by e.g. RCA. Thick grey element illustrate binding site for a detection oligonucleotide after amplification by RCA and the black elements represent a primer binding site for RCA or vice versa.

FIG. 12 shows combinations of endonucleases which combinations are considered unique for the target organisms Listeria, Campylobacter, Pseudomonas, Salmonella, and Staphylococcus.

Figure 13:
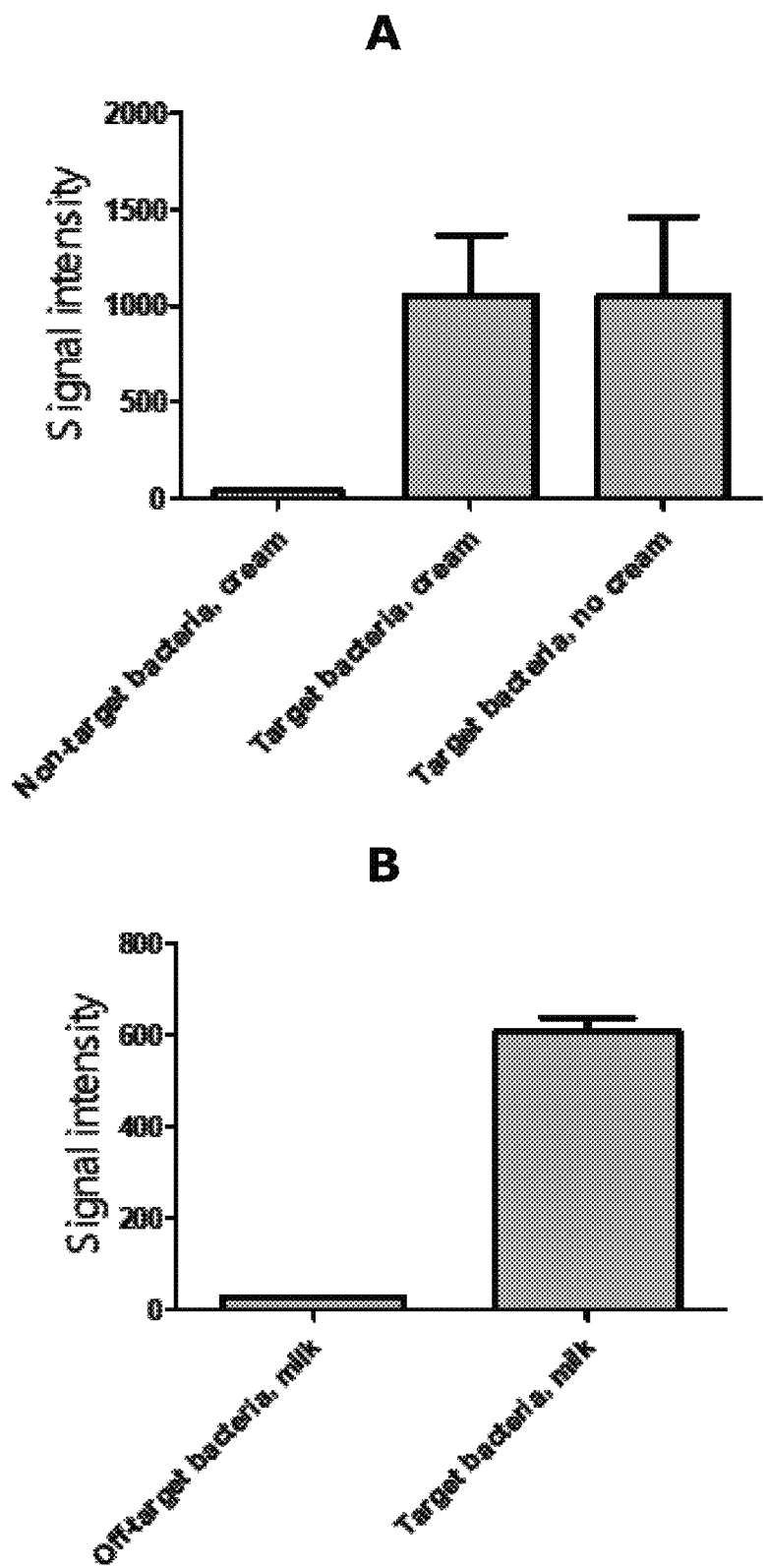

FIG. 13 shows non-target bacteria (DH5α) or target bacteria (RY13) lysed and analyzed in the presence or absence of A) cream or B) milk.

Figure 14:
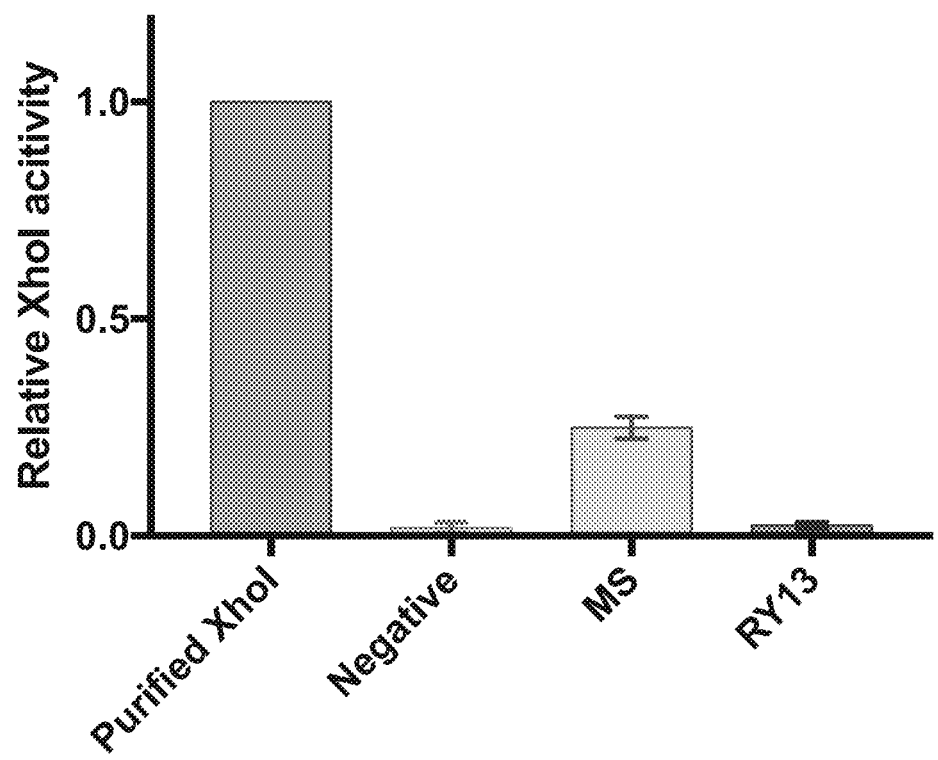

FIG. 14 shows XhoI activity in samples incubated with purified XhoI, water (negative control), M. smegmatis extract (MS) and extract from the *E. coli* bacterium RY13 using LNA containing primer. The results are the average from three repetitions, each normalized to the positive control with purified XhoI.

Figure 15:
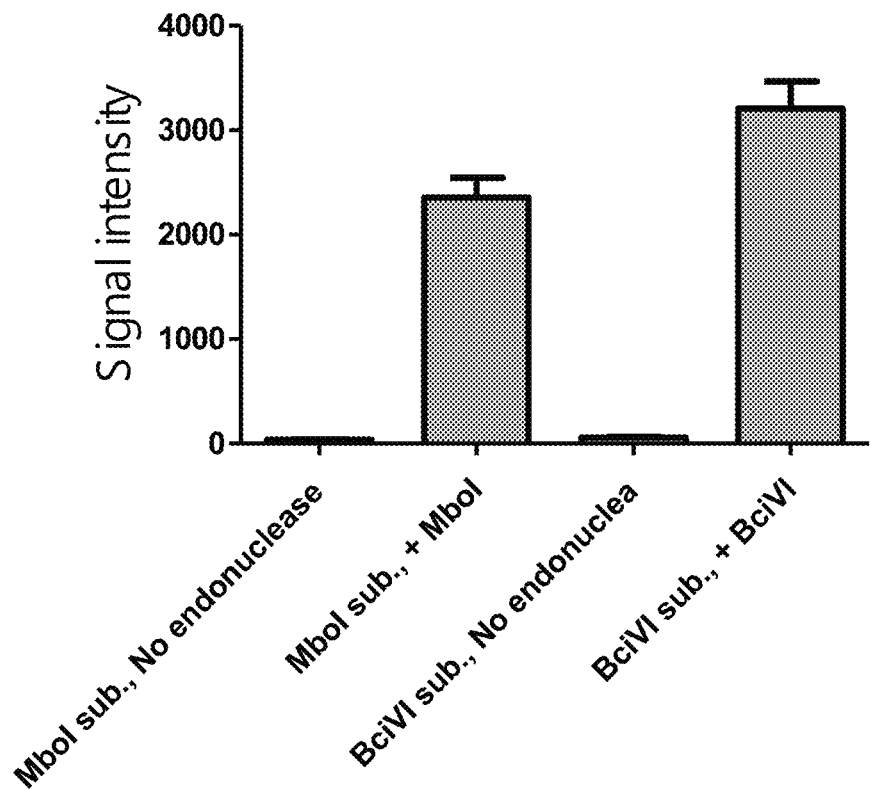

FIG. 15 shows the results of incubating the MboI substrate with or without purified MboI, and BciVI substrate incubated with or without purified BciVI.

Figure 16:
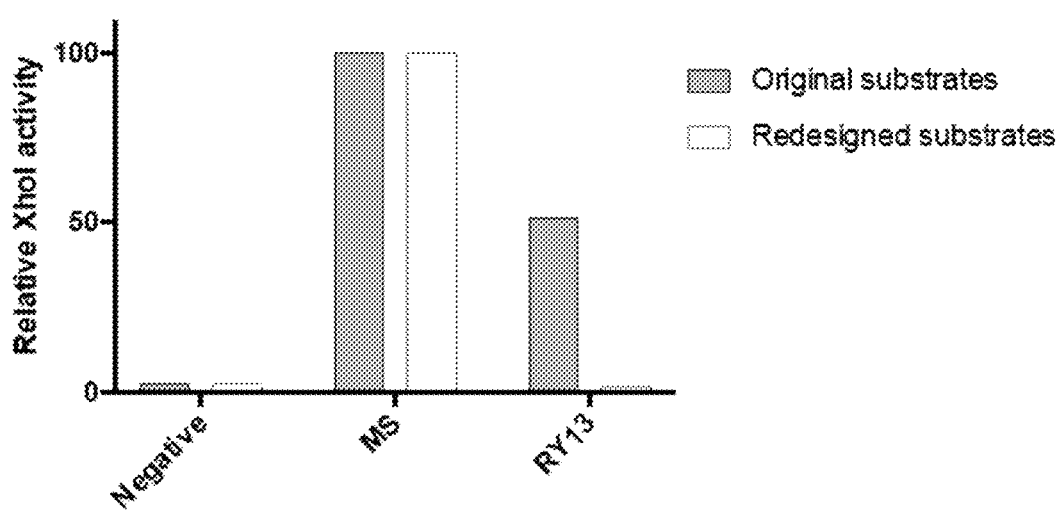

FIG. 16 shows XhoI activity measured in MS and RY13 with the protocol described in example 1. XhoI activity was measured using original substrates (grey) with identical sequences in the stem, and using redesigned substrates (white) with non-identical stems.

FIG. 17 shows titration curves with decreasing amounts of RY13 bacteria and *Mycobacteria smegmatis*. A) Detection of decreasing amounts of RY13 bacteria extracts. B) Detection of decreasing colony forming units (CFU) of *M. smegmatis* with the protocol using DNA primer. C) Detection of decreasing colony forming units (CFU) of *M. smegmatis* with the protocol modified with LNA primer. Neg: negative control without bacteria. HI: Control with heat-inactivated extract (HI).

Figure 18:
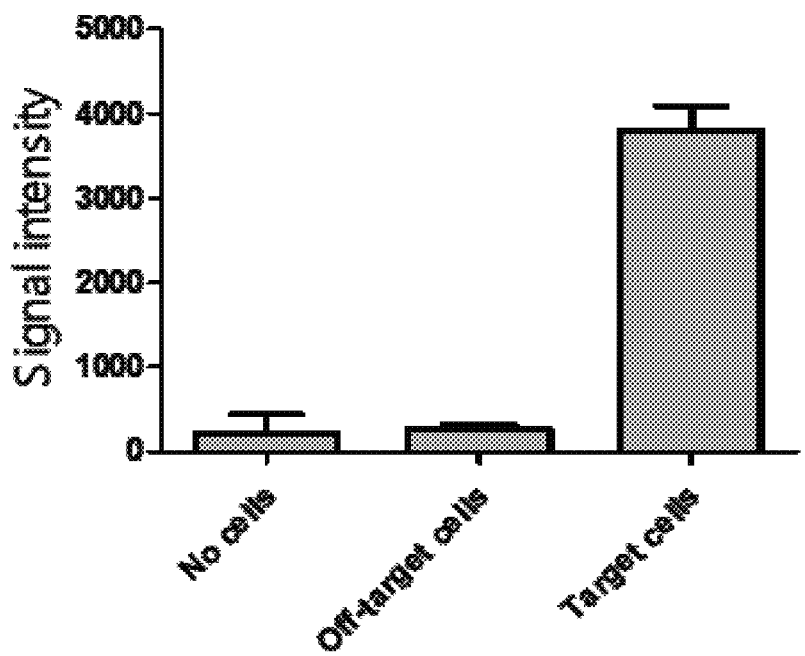

FIG. 18 shows detection of *E. coli* cells (Off target: DH5-alpha and Target: RY13 bacteria) in a one-step procedure.

The present invention will now be described in more detail in the following.

DETAILED DESCRIPTION OF THE INVENTION

Definitions

Prior to discussing the present invention in further details, the following terms and conventions will first be defined:
Restriction Endonuclease In the present context a "restriction endonuclease", "restriction enzyme", or just "endonuclease" refer to an enzyme that cleaves DNA into fragments at or near specific recognition sites within the molecule known as cleavage sites (or restriction sites). Restriction endonuclease are commonly classified into four types, which differ in their structure and whether they cut their DNA substrate at their recognition site, or if the recognition and cleavage sites are separate from one another. To cut DNA, all restriction endonucleases make two incisions, once through each sugar-phosphate backbone (i.e. each strand) of the double stranded DNA. Non-limiting examples of restriction endonuclease activity, which may be determined by the present invention, are EcoRI, PstI, XhoI, and SacII, or isoschizomers thereof (see also example 3). In a preferred embodiment of the invention, the endonuclease are Type II enzymes, which cut DNA at defined positions close to or within their recognition sequences.

Isoschizomers are pairs of restriction endonucleases specific to the same recognition sequence. For example, SphI (CGTAC/G) and BbuI (CGTAC/G) are isoschizomers of each other. The first enzyme discovered which recognizes a given sequence is known as the prototype; all subsequently identified enzymes that recognize that sequence are isoschizomers. Isoschizomers are isolated from different strains of bacteria.

Thus, in the present context, when a method according to the invention e.g. refers to detection of XhoI, PstI and SacII endonuclease activity, it is to be understood as also relate to detection of isoschizomers of these endonucleases.

In an embodiment, of the present invention, the restriction endonucleases are not topoisomerases, such as type I and type II topoisomerases, more specifically not a type IA, a type IB, a type IC, a type IIA, or a type IIB topoisomerase.
Sequence Identity In the present context, the term "identity" is here defined as the sequence identity between oligonucleotides at the nucleotide, base level.

Thus, in the present context "sequence identity" is a measure of identity between nucleic acids at nucleotide level. The nucleic acid sequence identity may be determined by comparing the nucleotide sequence in a given position in each sequence when the sequences are aligned. To determine the percent identity of two nucleic acids, the sequences are aligned for optimal comparison purposes (e.g., gaps may be introduced in the sequence of a first amino acid or nucleic acid sequence for optimal alignment with a second amino or nucleic acid sequence). The nucleotides at corresponding nucleotide positions are then compared. When a position in the first sequence is occupied by the same nucleotide as the corresponding position in the second sequence, then the molecules are identical at that position.

The percent identity between the two sequences is a function of the number of identical positions shared by the sequences (i.e., % identity=# of identical positions/total # of positions (e.g., overlapping positions)×100). In one embodiment, the two sequences are the same length. In another embodiment, the two sequences are of different length and gaps are seen as different positions. One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention.

To obtain gapped alignments for comparison purposes, Gapped BLAST may be utilized.

Alternatively, PSI-Blast may be used to perform an iterated search, which detects distant relationships between molecules. When utilising the NBLAST, XBLAST, and Gapped BLAST programs, the default parameters of the respective programs may be used. See http://www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

An embodiment of the present invention thus relates to sequences of the present invention that has some degree of sequence variation
Oligonucleotide In the present context, an oligonucleotide is a sequence of DNA (or RNA) nucleotide residues that form a molecule. Oligonucleotides can bind their complementary sequences to form duplexes (double-stranded fragments) or even fragments of a higher order. Oligonucleotides can be on a linear form, but also exist as circular oligonucleotide molecules, such as single stranded circular DNAs. When referring the length of a sequence, reference may be made to the number of nucleotide units or to the number of bases. Furthermore, the typical DNA or RNA nucleotides may be replaced by nucleotides analogues such as 2'-O-Me-RNA monomers, 2'-O-alkyl-RNA monomers, 2'-amino-DNA monomers, 2'-fluoro-DNA monomers, locked nucleic acid (LNA) monomers, arabino nucleic acid (ANA) monomers, 2'-fluoro-ANA monomers, 1,5-anhydrohexitol nucleic acid (HNA) monomers, peptide nucleic acid (PNA), and morpholinoes. In the present context, the oligonucleotide should be possible to amplify by e.g. RCA or PCR. Thus, preferably the oligonucleotide is DNA.

Stem-Loop Structure

In the present context the term "Stem-loop structure", refers to intramolecular base pairing that can occur in single-stranded DNA. The structure is also known as a "hairpin" or "hairpin loop". It occurs when two regions of the same strand, usually complementary in nucleotide sequence when read in opposite directions, base-pair to form a double helix that ends in an unpaired loop.

Method for Screening for Nuclease Activity

As described above, there is a need for methods, which can detect enzyme activities in different formats. Thus, an aspect of the invention relates to a method for screening for endonuclease activity in a sample, the method comprising
  a) providing a sample (S) to be analyzed;
  b) adding to the sample (S) at least one first oligonucleotide (1), to obtain a first reaction composition, the at least one first oligonucleotide (1) comprising a hairpin structure, wherein the stem of said hairpin structure comprises a first cleavage site (2) for a first endonuclease;
  c) adding a ligase to the first reaction composition obtained in b), to circularize at least the first oligonucleotide (1) if a endonuclease present in the sample (S) have cleaved the cleavage site (2) in the first oligonucleotide (1), wherein the produced circularized molecules (3) comprise part of stem-loop structures of the first oligonucleotide (1) after endonuclease cleavage;
  d) performing an amplification reaction using the at least first circularized oligonucleotides (3) as template, such as by LAMP, RCA or PCR; and
  e) detecting the amplified product from step d), thereby determining endonuclease activity in said sample.

The format where just one oligonucleotide (1) is used in the method of the invention, is further schematically outlined in FIG. 9.

The sample may have different origins. Thus, in an embodiment, the sample is a biological sample, such as selected from the group consisting of tissue samples, saliva, blood, food samples, surface swipes, such as from catheters, environmental sample, such as liquid, water, soil, air, plant samples, such as seeds. In another embodiment, the sample is a dairy sample such as milk or cream. In example 9, *E. coli* is detected in milk and cream.

In an embodiment, said biological sample is selected from the group consisting of food, such as meat, feed, plants, such as vegetables and fruit, fish, and eggs.

The method is considered particular relevant for the detection of bacteria, and in particular viable bacteria in a sample. Thus, in another embodiment, the presence of nuclease activity is indicative of (viable) microorganisms, such as bacteria in said sample, preferably indicative of viable bacteria, and even more preferably viable pathogenic bacteria. As shown in example 6, the method of the invention is able to distinguish between live and dead bacteria. In many sample formats, e.g. food samples the presence of dead bacteria may not constitute a risk factor. In yet an embodiment, said bacteria are selected from the group consisting of *listeria, Pseudomonas, Salmonella, Campylobacter, E. coli, Staphylococci*, MRSA, *Mycobacteria* such as *M. Tuberculosis* and *M. smegmatis, Streptococcus, Neisseria, Klepsiella,* and *Vibrio*.

The method of the invention may be designed in different ways, as outlined schematically in FIGS. 8-11). As outlined above the method may be performed with just one oligonucleotide (1), which can be circularized (FIG. 9) and subsequently amplified and detected e.g. by RCA. To improve sensitivity and specificity it may be advantageous to use a format, which employs two oligonucleotides (1, 4) (FIG. 11). In examples 1 to 7 such a format has been tested. Thus, in an embodiment, at least one further second oligonucleotide (4) is added to the sample in step b), wherein said second oligonucleotide (4) comprises a hairpin structure, wherein the stem of said hairpin structure comprises a cleavage site (2) for said first endonuclease. Thus, both oligonucleotides comprise a cleavage site for the same endonuclease. In yet an embodiment the first oligonucleotide (1) and the second oligonucleotide (4) are different in sequence.

Since the loop structures of the oligonucleotides are primarily single-stranded different functionalities may be added to these parts. Thus, in yet an embodiment, said first oligonucleotide (1) and said second oligonucleotide (4) have different loop sequences. As can be seen in the figures and examples one loop sequence may be used as a primer binding sequence and the other loop sequence may be used for binding of the detection probe (after amplification).

In a preferred embodiment, and, as also outlined in the examples and figures, the first oligonucleotide (1) and/or second oligonucleotide (4) are single stranded linear oligonucleotides (when denatured) able to form a hairpin structure and comprising a loop, a stem and two ends.

The stems of the oligonucleotides may also differ in sequence. Thus, in an embodiment said first oligonucleotide (1) and said second oligonucleotide (4) have different stem sequences. The stems of course still have identical cleavage sites for endonucleases (2). By having non-identical sequences on one or both sides of the cleavage sites for the endonuclease (2), unintentional endonuclease activity in both oligonucleotides (1, 4) is minimized. In example 12, off-targets effects are minimized by redesigning one of the two substrates.

In an embodiment, said first oligonucleotide (1) and said second oligonucleotide (4) have identical stem sequences and different loop sequences.

In yet an embodiment, in circulation step c) said first oligonucleotide (1) and said second oligonucleotide (4), if a endonuclease is present in the sample (S) have cleaved the cleavage site (2) in the first oligonucleotide (1) and the cleavage site (2) in the second oligonucleotide (4), can form a circular oligonucleotide product (5) comprising part of the stem-loop structure of the first oligonucleotide (1) and part of the stem-loop structure of the second oligonucleotide (4) after endonuclease cleavage. This step is also illustrated in FIG. 11. This "two-oligonucleotide" format of the invention is a preferred method of the invention.

In yet an embodiment, said first oligonucleotide (1) and said second oligonucleotide (4) are added simultaneously, e.g. from a mixed composition of said first oligonucleotide (1) and said second oligonucleotide (4).

In a different embodiment of the invention, the ligation step is aided by a support oligonucleotide (10), which may be added in step b) and/or c). Such support oligonucleotide may facilitate hybridization by bridging the 5'-end and the 3'-end of said oligonucleotide (1) after endonuclease cleavage. This method is further illustrated in FIG. 10.

Different microorganisms, and in particular bacteria, express different unique combinations of endonuclease primarily as a defense system. It is therefore important to be able to detect different endonuclease activities. Thus, in an embodiment, the first cleavage site (2) for a first endonuclease is selected from the group consisting of restriction sites specific for EcoRI, PstI, XhoI, SacII, MboI, Lmo911II, BciVI, HaeIII, NlaIII, HphI, AvaII, PvuII, XmaIII, Fnu4HI, ScrFI, MtuHN878II and SmlI, and isoschizomers thereof, preferably isoschizomers thereof.

It is noted that the endonuclease cleavage may create a 5'-overhang cleavage site, a 3'-overhang cleavage site or a blunt end cleavage site. Preferably, the endonuclease cleavage generates a 5'-overhang cleavage site or a 3'-overhang cleavage site, since this will likely increase the specificity.

It may also be advantageous to detect the presence of more than one endonuclease in a sample. Such multiplexing may be performed in the same reaction vessel or in parallel. Thus, in an embodiment, method further comprises screening said sample for nuclease activity of at least one further nuclease, using one or more further oligonucleotides (7, 8) comprising a hairpin structure, wherein the stem of said hairpin structure comprises a second cleavage site (6) for a second endonuclease. As also outlined above such multiplexing may be performed using the "one oligonucleotide" system according to the invention or the "two oligonucleotide" system of the invention. Again, these methods are schematically outlined in FIGS. 9-11.

The oligonucleotides to be employed in the method of the invention may of course have different lengths. Thus, in an embodiment said oligonucleotides (1, 2, 7, 8) have a length in the range 30-120 nucleotides, such as 40-105 nucleotides.

The length of the loop region may also vary. Thus in an embodiment, the loop region of said oligonucleotides (1, 2, 7, 8) have a length in the range 10-100 nucleotides, such as 10-50, or such as 10-25 nucleotides. As previously mentioned the length of the loop region should accommodate hybridization of primers or detection probes (or both) under normal hybridization conditions.

In yet an embodiment, said oligonucleotides (1, 2, 7, 8) consist of a stem-loop structure and has a length in the range 30-120 nucleotides.

In yet a further embodiment, the loop region of said oligonucleotides comprise a binding site for a primer, e.g. for PCR amplification or RCA amplification.

In another embodiment, the loop region of said oligonucleotides comprises a sequence identical to a detection oligonucleotide, wherein said detection oligonucleotide is complementary to an amplification product by RCA of said circularized oligonucleotides of step e).

The stem loop region of the oligonucleotides may also vary. Thus, in an embodiment, the (double stranded) stem region of said oligonucleotides have a length in the range 10-60, such as 10-50 nucleotides, such as 20-40 nucleotides.

In yet an embodiment, the stem region comprises at least 2 base pairs on each site of said cleavage site, such as at least 3 base pairs on each site, such as at least 4 base pairs on each site, and/or such as in the range 4-30 base pairs, such as 10-30 base pairs on the site towards the loop structure. By having enough base pairing after endonuclease cleavage the oligonucleotide is still able to form a stable stem-loop structure, even if the stem has been shortened The present invention also provides specific oligonucleotides. Thus, in an embodiment, said first oligonucleotide (1) is selected from the group consisting of
a) a polynucleotide selected from the group consisting of SEQ ID NO: 1-8 and 13-22; or
b) a polynucleotide having at least 80% sequence identity with the polynucleotides of a), with the proviso that a restriction site and a stem-loop structure is maintained.

In yet an embodiment, said second oligonucleotide (4) is selected from the group consisting of
a) a polynucleotide selected from the group consisting of SEQ ID NO: 1-8 and 13-22; or
b) a polynucleotide having at least 80% sequence identity with the polynucleotides of a), with the proviso that a restriction site and a stem-loop structure is maintained.

When two oligonucleotides are used in the method of the invention, it is of course important that they can form a dimer structure after endonuclease cleavage. Thus, in yet a further embodiment, said first oligonucleotide (1) and said second oligonucleotide (4) are selected from the following combinations:
a) SEQ ID NO: 1 and SEQ ID NO: 2;
b) SEQ ID NO: 3 and SEQ ID NO: 4;
c) SEQ ID NO: 5 and SEQ ID NO: 6;
d) SEQ ID NO: 7 and SEQ ID NO: 8;
e) SEQ ID NO: 13 and SEQ ID NO: 14;
f) SEQ ID NO: 15 and SEQ ID NO: 16;
g) SEQ ID NO: 1 and SEQ ID NO: 17;
h) SEQ ID NO: 3 and SEQ ID NO: 18;
i) SEQ ID NO: 15 and SEQ ID NO: 19;
j) SEQ ID NO: 13 and SEQ ID NO: 21; and
k) SEQ ID NO: 20 and SEQ ID NO: 22;
or
l) oligonucleotides of said combinations of a) to k) having at least 80% sequence identity with SEQ ID NO: 1-8 and 13-22, with the proviso that a restriction site and a stem-loop structure is maintained.

Thus, it is to be understood that in an embodiment of the invention a certain level of sequence diversity is foreseen.

It may be an advantage that the oligonucleotides cannot be degraded by e.g. exonucleases or can be ligated without first being cleaved by the intended endonuclease. Thus, in an embodiment, the first oligonucleotide (1) and/or second oligonucleotide (4) (and/or (7) and (8)) are blocked at the 5'-end and/or the 3'-end, preferably blocked at the 5'-end and the 3'-end to minimize undesired ligation reactions and/or exonuclease activity on the nucleotides. In a related embodiment, the blockings are selected from the group consisting of amines, biotin, and Digoxigenin.

Blocking may also as an alternative to ligation blockage (or in addition to) be blocked at the amplification stage to prevent amplification of circularized but uncleaved circles. This could be done by including in the oligonucleotides to be cleaved, nucleotides which cannot be amplified (and thus block the polymerase). Such nucleotides should be positioned at the side of the cleavage site (2) facing away from the loop structure. Such nucleotides could be positioned at just one strand or both strands facing away from the loop structure. Examples of such nucleotides are hexaethylene glycol modification, but some polymerases are also blocked by PNA's and LNA etc. Thus, in an embodiment, the oligonucleotide (1, 4, 7, 8) comprises one or more nucleotides (or linkers) making the oligonucleotide resistant to amplification by a polymerase, wherein said one or more nucleotide is positioned on one strand or both strands facing away from the loop structure. In yet an embodiment, said one or more nucleotide or linker is selected from hexaethylene glycol modifications, PNA's, LNA's, etc. Without being bound by theory, the different type of blockings (both ligation and amplification blocking) may also prevent or limit exonuclease degradation.

It could also be envisioned that one or more of the oligonucleotides comprising the cleavage site for the endonucleases (1, 4, 7, 8) are immobilized on a solid support. Thus, in an embodiment, said first oligonucleotide is (and/or 4, 7, 8) immobilized on a surface. In a related embodiment, the surface is a solid support. In yet a related embodiment, the solid support is glass, paper, cardboard, sepharose, agarose, plastic, metal, silicon, ceramics and latex. In yet a further embodiment, the solid support is coated with maleic anhydride.

Some of the steps of the method of the invention may be performed simultaneously. Thus, in an embodiment step b) and c) are performed simultaneously, so that said ligase is added to the sample together with the at least first oligonucleotide (1). This is also shown in example 7 and 15. In another embodiment, said ligase is selected from the group consisting of T4 DNA ligase, Pfu ligase, Taq ligase, T7 ligase, *E. coli* ligase, preferably T4 DNA ligase.

The skilled person would know that other components may be added to the reaction mixture to improve enzyme activity. Thus, in an embodiment, said ligation step is performed in a reaction environment allowing ligation, such as the presence of ATP and Mg.

It could also be envisioned that steps b) to d) could be performed simultaneously. Thus in an embodiment, step b), step c) and step d) are performed simultaneously, so that said circularization, ligation and amplification is performed simultaneously. In a related embodiment, oligonucleotides, ligase, primer(s), polymerase are added simultaneously in a reaction environment allowing ligation and amplification (see also example 15).

It could also be envisioned that steps b) to e) could be performed simultaneously. Thus, in yet an embodiment, a detection oligonucleotide (9) is also added, allowing steps b) to e) to be performed simultaneously. In such an instance, a molecular beacon may be used as detection oligonucleotide (see SEQ ID NO's: 11 and 12) (see also example 15).

The method of the invention is especially suited for in vitro use. Thus, in an embodiment, said method is for in vitro and/or ex vivo use. In a related embodiment, said method is for in vitro use for the determination of endonuclease activity.

The amplification step d) may be performed in different ways. Thus, in an embodiment, said amplification reaction d) is performed by a method selected from the group consisting of PCR, Rolling Circle Amplification (RCA), real-time-PCR, Southern blotting, quantitative PCR (qPCR), restriction fragment length dimorphism-PCR (RFLD-PCR), primer extension, DNA array technology, LAMP and isothermal amplification. In a preferred embodiment RCA is performed. In examples 1-7, 9-12 and 14-15 RCA has been used.

In yet an embodiment, said method is performed by RCA, where a primer is complementary to at least part of the loop region of the first oligonucleotide (1) or second oligonucleotide (4). In yet a further embodiment, said primer is coupled to a solid support.

The primer may also be positioned in other regions than the loop region in order to increase the specificity of the assay. Such primer may be designed for rolling circle amplification (RCA). Such primer may anneal across the fusion site generated by fusion of the two substrate-molecules. This means that RCA only occurs when the two hairpin substrates have been specifically digested and joined together. Since such primer has to anneal in a double-stranded region it may be an advantage to add e.g. 'locked nucleic acids' (LNA) in both the 5'-end and the 3'-end of the primer, which enhances hybridization. This could be 1-5 LNA's at each end, such as 1-4, 1-3, or 1-2 or 1 LNA at each end. Such a design is used in example 10.

Thus, in an embodiment, said primer is designed to hybridize to the stem region of the produced circularized molecules (3), wherein the primer hybridizes to neighboring regions in the stem originating from different cleaved (and ligated) first oligonucleotides (1). In yet an embodiment, the primer comprises 1-5 artificial nucleotides enhancing hybridizations (such as LNA) at each end such as 1-4, 1-3, or 1-2 or 1 nucleotide (such as LNA) at each end.

Phrased in another way, the oligonucleotides denoted 1 and 4 (with reference to FIG. 11) is cleaved by the target endonuclease(s) recognizing the target sites (2). This removes a ligation block (asterics) allowing ligation and formation of a circular product (3) containing a fusion site. The circular substrate is subjected to RCA and the product detected by hybridization to a probe spanning the fusion site and hence specific to RCA products enabled by cleavage dependent ligation. The probe contains LNA nucleotides (other nucleic acid analogues might be envisioned). The probe may be labeled with a detectable entity such as a fluorophore.

In an embodiment, the two fusing substrate molecules (1,4) are different from each other.

In another embodiment, the LNA probe functions as a primer for the RCA reaction as well as a detection probe.

In yet another embodiment, the LNA probe is not labeled and only serves as primer for the RCA reaction. The product is then visualized using the normal detection oligonucleotides.

The amplification product can be detected in different ways. Thus, in another embodiment, said RCA is detected by hybridizing a detection oligonucleotide (9) to the amplification product, wherein said detection oligonucleotide hybridizes to a single stranded region of said RCA product, such as e.g. the detection oligonucleotide (9) being identical to at least part of the loop region of said first oligonucleotide. The detection oligonucleotide can be linear or e.g. a molecular beacon. Non-limiting examples of detection oligonucleotides are provided as SEQ ID NO's: 10-12+23-24.

In an embodiment, the detection oligonucleotide (9) is detectably labelled with one or more fluorescent dyes, radioactive nucleotides or biotinylated nucleotides, or wherein the detection oligonucleotide is detectably labelled by being coupled to an enzyme, which enzyme is capable of converting a substrate into a detectable product. In yet a further embodiment, said detection oligonucleotide is a molecular beacon, such as SEQ ID NO: 11, or a linear labelled oligonucleotide such as SEQ ID NO: 10.

In another embodiment, said detection step e) is performed by a method selected from the group consisting of fluorescence, gels, radioactivity, electrochemistry, colorimetric, chemilumiscence, and magnetism.

It is however also possible to use PCR. Thus, in another embodiment, said amplification method is performed by PCR, where one primer is complementary to at least part of the loop region of the first oligonucleotide (1) and where a second primer is identical to at least part of the loop region of the second oligonucleotide (4). This embodiment is with the proviso that the method of the invention relates to the embodiment where two different oligonucleotides are used, e.g. as illustrated in FIG. 11.

In the case that the "one oligonucleotide" method of the invention as e.g. illustrated in FIG. 9 are used, PCR can also be used for amplification. In the method illustrated in FIG. 9, primers could be positioned in the loop regions and where a PCT product will only be generated if a circularized product has been generated. Thus, the PCR product should be generated "across" the ligation site.

As previously mentioned, the method can be multiplexed to determine the activity of multiple endonucleases in a sample. By multiplexing the method, viable specific microorganisms may be identified. As also illustrated in example 8 and FIG. 12, specific combinations of endonucleases have been identified which are considered specific for a particular microorganism, such as a bacteria.

Thus, in an embodiment of the method, the detection of endonuclease activity of:
XhoI, PstI and/or SacII or isoschizomers thereof is indicative of viable *Pseudomanas* in said sample, preferably *Pseudomonas aeruginosa*;
MboI, Lmo911II and/or BciVI or isoschizomers thereof is indicative of viable *Listeria* in said sample, preferably *Listeria monocytogenes*;
HaeIII, NlaIII, and/or HphI or isoschizomers thereof is indicative of viable *Campylobacter* in said sample, preferably *Campylobacter jejuni*; or
AvaII, PvuII and/or XmaIII or isoschizomers thereof is indicative of viable *Salmonella* in said sample, preferably *Salmonella enterica*; or
Fnu4HI, ScrFI, and/or SmlI or isoschizomers thereof is indicative of viable *Staphylococcus* in said sample, preferably *Staphylococcus aureus*; or
MtuHN878II is indicative of viable *mycobacteria* belonging to the *Mycobacterium tuberculosis* complex in said sample.

In yet an embodiment of the method, the detection of endonuclease activity of:
Limo-set1: Lmo911, BciVI, and/or MboI or isoschizomers thereof;
Limo-set2: Lmo911, BciVI, and/or SalI or isoschizomers thereof;
Limo-set3: Lmo911, BciVI, and/or TseI or isoschizomers thereof;
Limo-set4: Lmo911, BciVI, and/or HaeIII or isoschizomers thereof;
Limo-set5: Lmo911, BciVI, and/or BbvII or isoschizomers thereof;
Limo-set5: Lmo911, MboI, and/or SalI or isoschizomers thereof;
Limo-set6: Lmo911, MboI, and/or TseI or isoschizomers thereof;
Limo-set7: Lmo911, MboI, and/or HaeIII or isoschizomers thereof; or
Limo-set8: Lmo911, MboI, and/or BbvII or isoschizomers thereof;
is indicative of viable *Listeria* preferably *Listeria monocytogenes*

In yet an embodiment of the method, the detection of endonuclease activity of:
Lisp-set1: Lmo911, BciVI, and/or BbvI or isoschizomers thereof; or
Lisp-set2: Lmo911, MboI, and/or BbvI or isoschizomers thereof.
is indicative of viable *Listeria* sp. (Lisp).

Thus, by inserting the recognition site (see FIG. 12) for one of the listed endonucleases or isoschizomers thereof in the stem of the hairpin structure of oligonucleotide(s) (1, 4) (as a first cleavage site (2)) the activity of these endonucleases can be determined by the methods of the invention. Again multiplexing can be performed (e.g. in parallel) to determine the activity of the relevant combinations.

In an embodiment, the cells are lysed e.g. using a Lysozyme before initiating or during the method of the invention.

In an embodiment, steps b)-c) are performed in a single step (see example 7). In another embodiment, steps b)-d) are performed in a single step. Thus, all relevant reagents may be present or added simultaneously. In example 15, data using such a process is presented. In yet an embodiment, the at least one further second oligonucleotide (4) is also present in this single step.

In yet another embodiment, the method is performed in a microfluidic chip setup/flow channel, such as a microfluidic chip comprising a serpentine channel. See also examples 7 and 15.

It is noted that in most instances isoschizomers of the listed endonucleases are determined, since it is preferably the activity of the endogeneous endonucleases, which is detected, and not purified commercially available enzymes.

Kit

The present invention also relates to a kit or kit of parts. Thus, an aspect of the invention relates to a kit comprising
a first container comprising a composition comprising at least one first oligonucleotide (1); the first oligonucleotide (1) comprising a hairpin structure, wherein the stem of said hairpin structure comprises a cleavage site (2) for a first endonuclease;
optionally, a second container comprising a composition comprising at least a second oligonucleotides (4), the second oligonucleotide (4) comprising a hairpin structure, wherein the stem of said hairpin structure comprises a restriction site (2) for the first endonuclease;
optionally, instruction for using said kit to determine the presence of endonuclease activity in a sample;
optionally, a third container comprising a ligase;
optionally, a fourth container comprising a polymerase;
optionally, a fifth container comprising one or more primers; and
optionally, a sixth container comprising one or more detection oligonucleotides (9).

In a preferred embodiment, the kit comprises both the first container and the second container. In another preferred embodiment, the oligonucleotide of the first container and the oligonucleotide of the second container is mixed in one (first container). In yet an embodiment, said first oligonucleotide (1) and said second oligonucleotide (4) is present in the same container. In yet an embodiment, said first oligonucleotide (1) and said second oligonucleotide (4) and said primer is present in the same container.

As previously mentioned, the method may be multiplexed (e.g. in parallel or in the sample reaction vessel). Thus, in an embodiment, the kit further comprises
A seventh container comprising a composition comprising at least a third oligonucleotide (7), the third oligonucleotide (7) comprising a hairpin structure, wherein the stem of said hairpin structure comprises a restriction site (5) for a second endonuclease;
optionally, an eight container comprising a composition comprising at least a fourth oligonucleotide (8), the eight oligonucleotide (8) comprising a hairpin structure, wherein the stem of said hairpin structure comprises a restriction site (5) for the second endonuclease.

Again further containers could be included if e.g. the activity of three different endonucleases should be determined as also outlined in FIG. 12.

In a preferred embodiment, the kit comprises a container comprising a ligase+e.g. buffers therefore.

In another preferred embodiment, the kit comprises a container comprising a polymerase+e.g. buffers therefore including dNTP's.

In yet a preferred embodiment, the kit comprises a container comprising one or more primers; and In yet another preferred embodiment, the kit comprises a container comprising one or more detection oligonucleotides (9).

In another embodiment, the first container may also comprise the primer and/or detection oligonucleotide, in such a way that al required oligonucleotides are in the same container. As previously mentioned the primer may also function as detection oligonucleotide.

In a further embodiment, said first container further comprises ligase, polymerase (preferably Phi29), and reagents therefore (such as dNTPs), e.g. all in a lysophilized form. (See example 15). In such a setup, a sample in solution could simply be added to the content of the first container to initiate the reaction.

Use of Kit

An aspect of the invention also relates to uses of the kit according to the invention to screen for the presence of viable (pathogenic) bacteria in a sample. In an embodiment, the bacteria is selected from the group consisting of Listeria, Campylobacter, Salmonella, Staphylococcus and Pseudomonas. In a related embodiment, the bacteria is selected from the group consisting of Pseudomonas aeruginosa, Listeria monocytogenes, Campylobacter jejuni, Salmonella enterica and Staphylococcus aureus. In yet a related embodiment, the bacteria is E. Coli. FIG. 12 shows endonucleases considered relevant to detect for these specific species.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1—Materials and Methods

DNA Oligonucleotides:
Oligonucleotides were purchased from LGC Biosearch Technologies
Primer binding sequence: Bold
Detection probe binding sequence: Underlining
Target enzyme binding site: Lower case letters Table 1

Substrate sequences (the target enzyme to which they are designed is mentioned in the end of the name)

| Oligo name | Sequence | SEQ ID NO |
|---|---|---|
| REN2-ID33-EcoRI | 5'-Amine-ATTTGACgaattcGTCGTATAGGAACTTCGAACGACTCG<u>CCTCAATG CACATGTTTGGCTCCC</u>GAGTCGTTCGAAGTTCCTATACGACgaattcG TCAAAT-Amine | 1 |
| REN2-PB-EcoRI | 5'-Amine-ATTTCCAgaattcTGGGTATAGGAACTTCGAACGACTCGACTGTGAA GATCGCTTATCGAGTCGTTCGAAGTTCCTATACCCAgaattcTGGAA AT-Amine | 2 |
| REN2-ID33-XhoI | 5'-Amine-ATTTGACctcgagGTCGTATAGGAACTTCGAACGACTCG<u>CCTCAATG CACATGTTTGGCTCCC</u>GAGTCGTTCGAAGTTCCTATACGACctcgag GTCAAAT-Amine | 3 |
| REN2-PB-XhoI | 5'-Amine-ATTTCCActcgagTGGGTATAGGAACTTCGAACGACTCGACTGTGA AGATCGCTTATCGAGTCGTTCGAAGTTCCTATACCCActcgagTGGA AAT-Amine | 4 |
| REN2-ID33-SacII | 5' Amine-ATTTGACccgcggGTCGTATAGGAACTTCGAACGACTCG<u>CCTCAATG CACATGTTTGGCTCCC</u>GAGTCGTTCGAAGTTCCTATACGACccgcgg GTCAAAT-Amine | 5 |
| REN2-PB-SacII | 5' Amine-ATTTCCAccgcggTGGGTATAGGAACTTCGAACGACTCGACTGTGA AGATCGCTTATCGAGTCGTTCGAAGTTCCTATACCCAccgcggTGG AAAT-Amine | 6 |
| REN2-ID33-PstI | 5' Amine-ATTTGACctgcagGTCGTATAGGAACTTCGAACGACTCG<u>CCTCAATG CACATGTTTGGCTCCC</u>GAGTCGTTCGAAGTTCCTATACGACctgcag GTCAAAT-Amine | 7 |
| REN2-PB-PstI | 5'-Amine-ATTTCCActgcagTGGGTATAGGAACTTCGAACGACTCGACTGTGA | 8 |

Table 1-continued

Substrate sequences (the target enzyme to which they are designed is mentioned in the end of the name)

| Oligo name | Sequence | SEQ ID NO |
|---|---|---|
| | AGATCGCTTATCGAGTCGTTCGAAGTTCCTATACCCActgcagTGGAAAT-Amine | |
| REN2-ID33-BciVI | 5'-Amine-ATTTGACgtatccaaataGTCGACTTCGAACGACTCGCCTCAATGCACATGTTTGGCTCCCGAGTCGTTCGAAGTCGACaaataggatacGTCAAAT-Amine | 13 |
| REN2-PB-BciVI | 5'-Amine-ATTTCCAgtatcattaaaTGGGACTTCGAACGACTCGACTGTGAAGATCGCTTATCGAGTCGTTCGAAGTCCCAtttaaaggatacTGGAAAT-Amine | 14 |
| REN2-ID33-MboI | 5'-Amine-ATTTGACgatcGTCGTATAGGAACTTCGAACGACTCGCCTCAATGCACATGTTTGGCTCCCGAGTCGTTCGAAGTTCCTATACGACgatcGTCAAAT-Am | 15 |
| REN2-PB-MboI | 5'-Amine-ATTTCCAgatcTGGGTATAGGAACTTCGAACGACTCGACTGTGAAGATCGCTTATCGAGTCGTTCGAAGTTCCTATACCCAgatcTGGAAAT-Amine | 16 |
| REN2B-PB-EcoRI | 5'-Amine-ATTCACTgaattcAGCGCTTAGGAGTGCATATACGATGCACTGTGAAGATCGCTTATGCATCGTATATGCACTCCTAAGCGCTgaattcAGTGAAT-Amine | 17 |
| REN2B-PB-XhoI | 5'-Amine-ATTCACTctcgagAGCGCTTAGGAGTGCATATACGATGCACTGTGAAGATCGCTTATGCATCGTATATGCACTCCTAAGCGCTctcgagAGTGAAT-Amine | 18 |
| REN2B-PB-MboI | 5'-Amine-ATTCACTgatcAGCGCTTAGGAGTGCATATACGATGCACTGTGAAGATCGCTTATGCATCGTATATGCACTCCTAAGCGCTgatcAGTGAAT-Amine | 19 |
| REN2B-PB-Lmo911 | 5'-Amine-ATTCACTCATCAGTGATCtagaagAGCGCTTAGGAGTGCATATACGATGCACTGTGAAGATCGCTTATGCATCGTATATGCACTCCTAAGCGCTcttctaGATCACTGATGAGTGAAT-Amine | 20 |
| REN2B-PB-BciVI | 5'-Amine-ATTCACTgtatcctttAAAAGCGCTGTGCATACGATGCACTGTGAAGATCGCTTATGCATCGTATGCACAGCGCTTTTaaggatacAGTGAAT-Amine | 21 |
| REN2-ID33-Lmo911 | 5'-Amine-ATTTGACGGTCACGAGtagaagGTCGTATAGGAACTTCGAACGACTCGCCTCAATGCACATGTTTGGCTCCCGAGTCGTTCGAAGTTCCTATACGACcttctaCTCGTGACCGTCAAAT-Amine | 22 |

Table 2

Other oligonucleotides

| RCA-Primer | 5'-Amine-CCAACCAACCAACCAA-ATAAGCGATCTTCACAGT-3' | 9 |
|---|---|---|
| Detection probe 1 | FAM-CCTCAATGCACATGTTTGGCTCC | 10 |
| Detection probe 2 (ID16) | 5'-CAL Fluor 590-GUAGACCUCAAUGCUGCUGCUGUACUAC,-3'-BHQ-2 (Black Hole Quencher-2), (2'OMe-RNA) | 11 |
| Detection probe 3 (ID33) | 5' FAM-AGCCACCUCAAUGCACAUGUUGGU,-31-BHQ1 (Black Hole Quencher-1), (2'OMe-RNA) | 12 |
| LNA FUSION XhoI | 5'-TYE665- +T+ACGACCT+C+G-3' ("+" indicates the nucleotide being an LNA) | 23 |
| LNA FUSION EcoRI | 5'-FAM- +C+TGAATTC+G+T-3' ("+" indicates the nucleotide being an LNA) | 24 |

Covalent Coupling of Amine Conjugated RCA-Primer to CodeLink Slide

The amine-coupled RCA primer (SEQ ID NO: 9) is coupled to Codelink slides (Surmodics) as described below:

The amine-couple oligonucleotide is diluted in 50 mM sodium-phosphate buffer, pH 8.5 to a final concentration of 5 μM. 5 μL of this solution is added to a small area (4×4 mm) of a CodeLink slide (marked using a hydrophobic PAP pen). The oligonucleotide conjugated area of the CodeLink slide is denominated the printed area.

The slide is incubated over night at room temperature in a humidity chamber with saturated salt.

Next day, the slide is processed as follows: 30 minutes in warm (50° C.) blocking buffer, 2×1 minute wash in water, 30 minutes in warm (50° C.) wash buffer 1, 2×1 minute wash in water. Let the slide air-dry.

Testing Purified Enzymes

Restriction endonucleases were purchased from Thermo Scientific (EcoRI) or New England Biolabs (all others).

For detection of EcoRI activity, 50 pmol of each of the two substrates REN2-ID33-EcoRI (SEQ ID NO: 1) and REN2-PB-EcoRI (SEQ ID NO: 2) were incubated for 1 h at 37° C. either with or without 10 units of EcoRI. The reaction was done in a reaction buffer containing 500 mM Potassium Acetate; 200 mM Tris-acetate; 100 mM Magnesium Acetate; and 1 mg/ml BSA (pH 7.9). The reaction volume was 50 μL. After incubation, the restriction endonuclease was inactivated by heating to 94° C. for 10 minutes. ATP was added to a final concentration of 10 mM and 1 unit of T4 ligase (Invitrogen) was added. The reaction mixture was then incubated over night at room temperature.

Next day, the ligase was inactivated by heating to 94° C. for 10 minutes. Unreacted substrate DNA was then removed by adding 20 units each of Exonuclease I and III (New England Biolabs). After incubation at 37° C. for 1 h the exonucleases were inactivated by heating to 94° C. for 10 minutes.

NaCl was added to the samples to a final concentration of 500 mM and 10 μL of the reaction mixture was placed on top on one of the printed areas of the CodeLink slide (see Covalent coupling of amine conjugated RCA-primer to CodeLink slide). The CodeLink slide was incubate at 37° C. for 1 h in a humidity chamber. Washed for 1 min in wash buffer 2, 1 min in wash buffer 3, and 1 min in 96% ethanol and air dried.

Rolling Circle Amplification:

Prepare RCA reaction mixture as suggested for the supplier of the Phi29 polymerase, Thermo Scientific. Add 10 μL of reaction mixture to each printed area. Incubate 1 h at 37° C. in a humidity chamber. Wash the slide for 1 minute in wash buffer 2, 1 minute in wash buffer 3, and 1 minute in 96% ethanol. Let the slide air dry.

Probe Hybridization:

A solution with 2×SSC, 20% formamide, 5% glycerol, and 0.2 μM of ID33 probe (FAM-CCTCAATGCA-CATGTTTGGCTCC) (SEQ ID NO: 10) was prepared. 10 μl was added to each printed area. The slide was then incubated for 30 min at 37° C. in humidity chamber, washed in wash buffer 2 for 15 min, washed in wash buffer 3 for 10 min, and washed in 99% ethanol for 1 min. After air-drying the slide was mounted using vectorshield without DAPI.

Visualization and Analysis:

Fluorescence labeled RCA products were visualized in a fluorescence microscope (Olympus IX73) and quantified by counting the number of signals per microscopic image frame using the ImageJ software. The results were obtained by counting the number of signals on 9 randomly picked microscopic pictures (277,3×234 μm$^2$) for each sample analyzed. The number of signals were counted using the ImageJ software.

Buffers:
10× Reaction Buffer (the Same as CutSmart® Buffer Sold by NEB):
  500 mM Potassium Acetate
  200 mM Tris-acetate
  100 mM Magnesium Acetate
  1 mg/ml BSA
  pH 7.9 (25° C.) adjust with Acetic Acid or KOH
Phi29 (Fermentas/Thermo Fisher Scientific (Cat. Number: EP0094)
  Storage Buffer for phi29 polymerase:
  50 mM Tris-HCl (pH 7.5),
  0.1 mM EDTA, 1 mM DTT, 100 mM KCl,
  0.5% (v/v) Nonidet P40, 0.5% (v/v) Tween 20 and 50% (v/v) glycerol.
  10× Reaction Buffer for phi29 polymerase:
  330 mM Tris-acetate (pH 7.9 at 37° C.),
  100 mM Mg-acetate, 660 mM K-acetate,
  1% (v/v) Tween 20, 10 mM DTT.
  20×SSC contains 3.0 M NaCl and 0.3 M sodium citrate, at pH 7.0.
  2× hybridization buffer: 40% Formamide, 4×SSC, 10% glycerol.
  Blocking buffer: 50 mM Ethanolamine, 0.1 M Tris (pH 9.0). Details: 12.11 g Trizma
  Base, 15.76 g Trizma HCl, 6 mL ethanol amine—add elga-water to 1.7 L and adjust pH to 9. Adjust volume to 2 L with elga-water.
  Wash buffer 1: 4×SSC; 0.1% SDS
  Wash buffer 2: 0.1M Tris-HCl (pH 7.5); 150 mM NaCl; 0.3% SDS
  Wash buffer 3: 0.1M Tris-HCl (pH 7.5); 150 mM NaCl; 0.05% Tween 20

Testing Model Bacteria Expressing EcoRI:

Bacteria were grown to an OD600 of 0.6. At this point they were harvested by centrifugation (4000×g for 15 min at 4° C.) and aliquots of 20 mg bacterial pellet (wet weight) were frozen and stored at −80° C.

One pellet was thawed on ice and resuspended in 1 mL lysis buffer (10 mM Tris-HCl (pH 7.5); 1 mM DTT; 19 mM NaF; 1 mM Beta Glycerophosphate (disodium salt); Roche proteases inhibitors cocktail, EDTA free (as described by supplier); 1 mM PMSF). The solution was incubated on ice for 1 h and sonicated for 10 times 10 seconds. After sonication the lysate was spun at 14000 rpm for 10 minutes in a standard bench top microcentrifuge.

The lysate was then incubated with DNA substrates (20 v % lysate) as described for purified enzymes above. Also the subsequent ligation, hybridization to the slides, RCA, hybridization to detection probe, microscopy; and data analysis was done as described above.

Microfluidics Enabled Lysis:

The bacteria to be analyzed was pelleted and resuspended in 20 mg/mL lysis buffer (10 mM Tris-HCl pH 7.5); 1 mM DTT; protease inhibitors). Lysozyme was added to a final concentration of 50 μg/mL. This is denoted the lysis solution.

Figure 7:
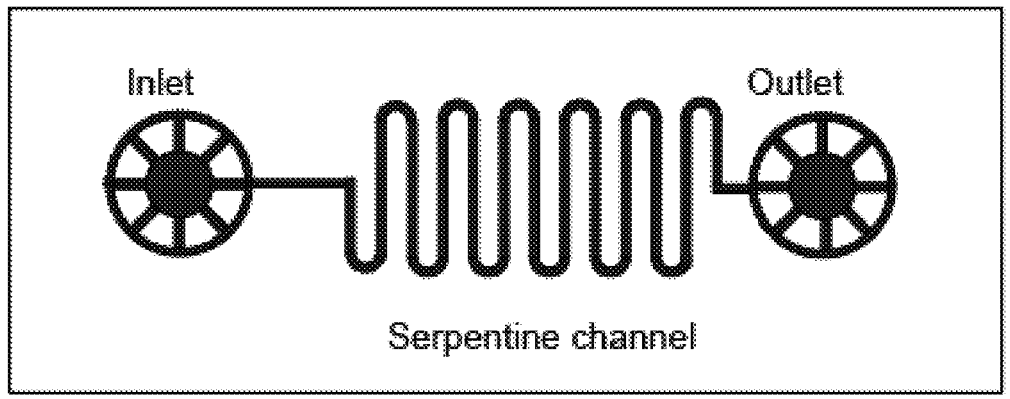
FIG. 7
Figure 8:
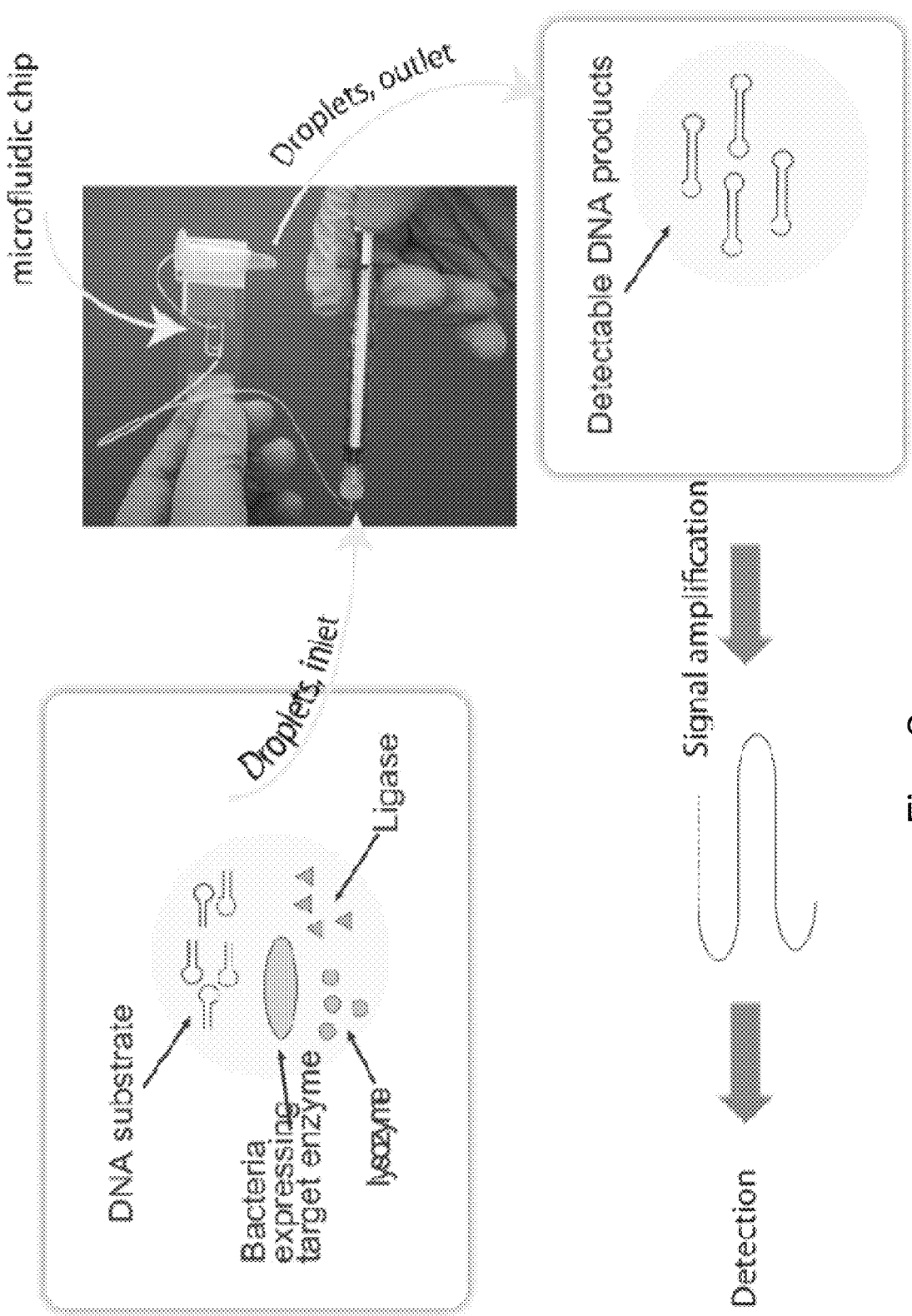

A reaction mixture consisting of 20 v % lysis solution; reaction buffer (final 1×); 10 mM ATP; and 1 unit/50 μL T4 ligase was prepared. 2× volume of oil (Pico-Surf (TM) 1, 10 ml, 2% in Novec 7500) was added and the emulsion vortexed for 1 minute. The formed emulsion was introduced into a syringe and passed through a microfluidic chip containing 1 inlet and 1 outlet separated by a serpentine channel (FIG. 7).

After passage through the serpentine channel the droplets generated during vortexing were collected in an Eppendorf tube.

The droplets were left for 1 h at room temperature and then broken by addition of 25 v % 1H,1H,2H,2H-perfluorooctanol. The reaction was allowed to continue over night at room temperature. Next day, the ligase was inactivated by heating to 94° C. for 10 minutes and the samples analyzed as described for purified enzyme.

Example 2—Detection of a Purified Target Enzyme (EcoRI)

Aim

Figure 1:
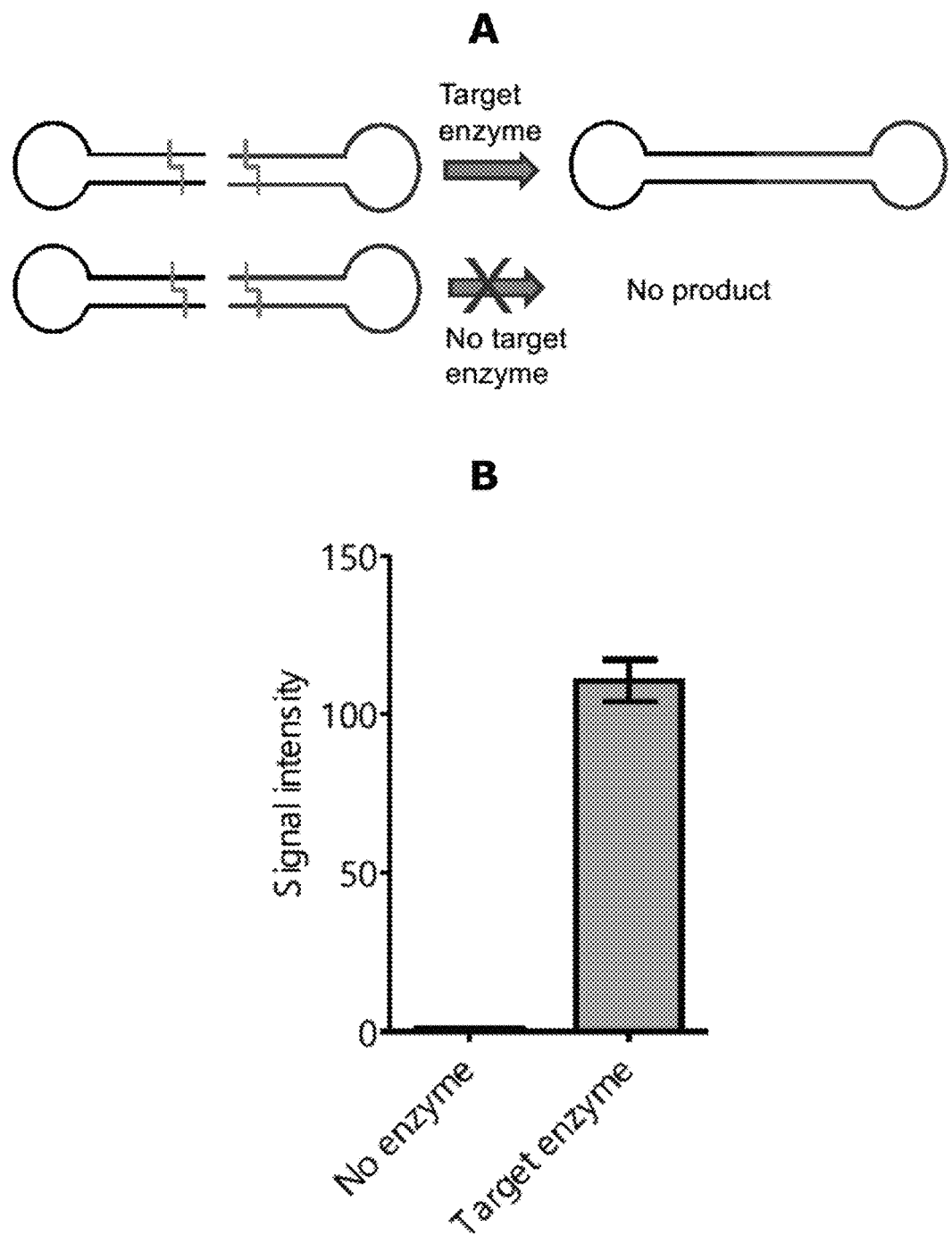
FIG. 1 shows detection of a Purified Target Enzyme (EcoRI). A: Detection of EcoRI activity is based on the endonuclease dependent fusion of two DNA elements that are both needed for detection. Without the RE dependent fusion, no detectable product will be formed. B: Proof-of-concept for RE detection was done using the model target enzyme EcoRI.

To validate the substrate design and the protocol, using a pilot experiment with EcoRI as a model target enzyme.
Materials and Methods
See example 1.
Results The two substrate molecules carrying the EcoRI cleavage sites (see materials and methods) were incubated with or without purified enzyme and subjected to the protocol as described in materials and methods (see also FIG. 1A). After counting the signals, the fold increase over background (no enzyme) was calculated. The number of signals was 110.5 times higher (std error 6.6) when the target enzyme was added than when no enzyme was added (FIG. 1B).
Conclusion This result clearly demonstrates the ability of the technology to detect endonuclease activity.

Example 3—Detection of Individual Target Enzymes is Specific

Aim of Example:

In order to test if the substrates are processed specifically by the target enzymes to which they are designed 4 different substrate systems were tested (carrying EcoRI, PstI, XhoI, or SacII cleavage sites) using two units (EcoRI, PstI, XhoI, and SacII) or 10 units (SacII) of their respective target enzyme or a panel of off target enzymes (2 units). See also table 1 in example 1.
Results:

Substrate sets carrying the ExoRI, XhoI, PstI, or SacII recognition sites were incubated with either their target enzyme or off target enzymes. The substrate designed to react with EcoRI (Sub. EcoRI) is specific for EcoRI among the enzymes tested. Likewise, the substrates for PstI, XhoI, and SacII are specific for their respective target enzymes (FIG. 2).
Conclusion:

These results clearly demonstrate that signals are obtained only when the purified enzyme is incubated with the substrates carrying the specific target site for that enzyme.

Example 4—Quantitative Detection of Pseudomonas Relevant Target Enzymes in Purified Form Aim of Example:

Based on the REBASE database (www.http://rebase.neb.com) we identified a putative set of enzymes for detection of Pseudomonas. This set consists of three enzymes that are isoschizomers of the commercially available restriction endonucleases XhoI, PstI and SacII. We used these three enzymes (purified) for testing if the technology is quantitative and hence usable for enumeration of bacteria.

Results

The indicated number of units of the indicated purified enzymes was incubated with the substrates carrying the recognition sites for the respective enzymes (FIG. 3). The incubation as well as the rest of the protocol was done as described in materials and methods (example 1).
Conclusion The above results clearly show that the technology of the invention is quantitative in nature.

Example 5—Detection of Target Enzyme EcoRI Expressed by a Model Target Bacteria

Aim of Example

Figure 4:
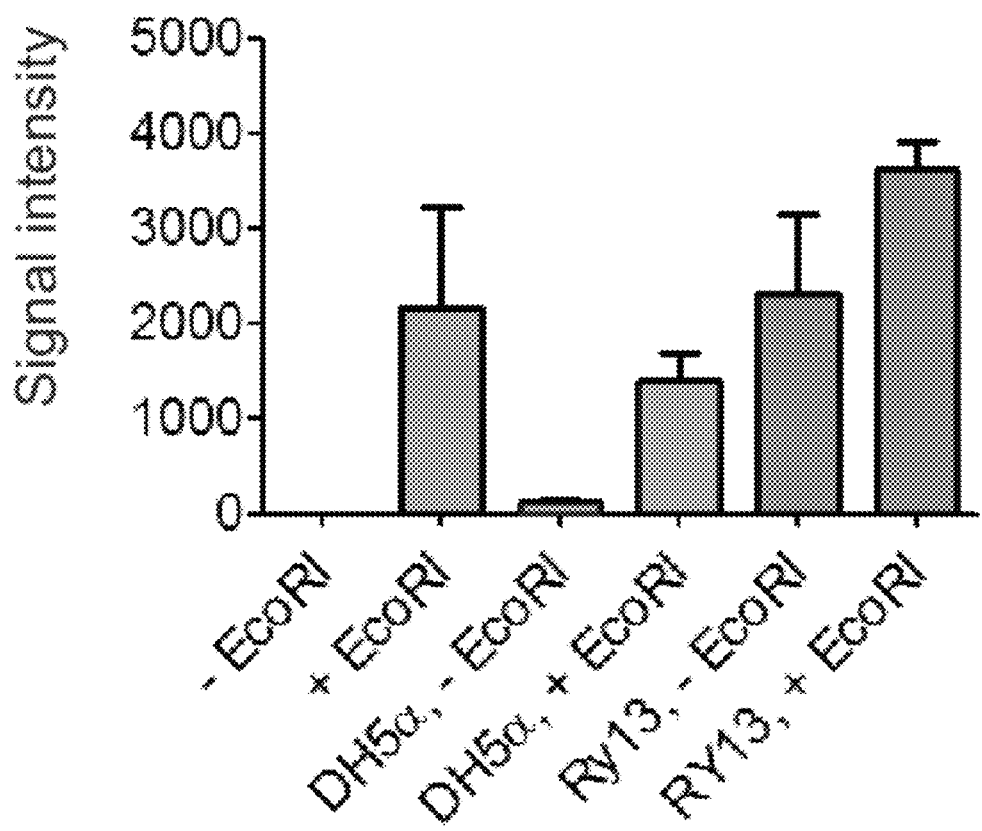
FIG. 4 shows detection of target enzyme EcoRI expressed by a model target bacteria. The method was able to discriminate between an E. coli strain that express EcoRI (RY13) and another E. coli strain that does not express EcoRI (DH5α). Purified EcoRI was spiked in the samples as indicated

To test if bacteria can be discriminated based on the expression of the restriction endonuclease EcoRI, substrates carrying a recognition site for EcoRI were incubated with lysate from E. coli either expressing (the strain RY13) or not expressing (the strain DH5-alpha) EcoRI.
Results Six types of samples were analyzed:
1) Samples with neither lysate nor purified enzyme added
2) samples with purified EcoRI added
3) samples with lysate of DH5-alpha cells added
4) samples with lysate of DH5-alpha cells added—together with purified EcoRI
5) samples with lysate of RY13 cells added
6) samples with lysate of RY13 cells added—together with purified EcoRI In the samples, where no purified enzyme or lysate from RY13 was added, no or very few signals were observed (column 1 and 3 in FIG. 4). If either purified EcoRI or lysate from EcoRI expressing cells (Ry13) was added (or both), signals were observed (column 2, 4 5, 6 in FIG. 4). The effect seems to be additive (compare column 5 and 6 in FIG. 4).
Conclusion Model E. coli bacteria DH5-alpha (not expressing EcoRI) and RY13 (expressing EcoRI) could be discriminated by the method of the invention based on the expression of EcoRI.

Example 6—Differentiation Between Dead and Living Bacteria

Aim of Example

Figure 5:
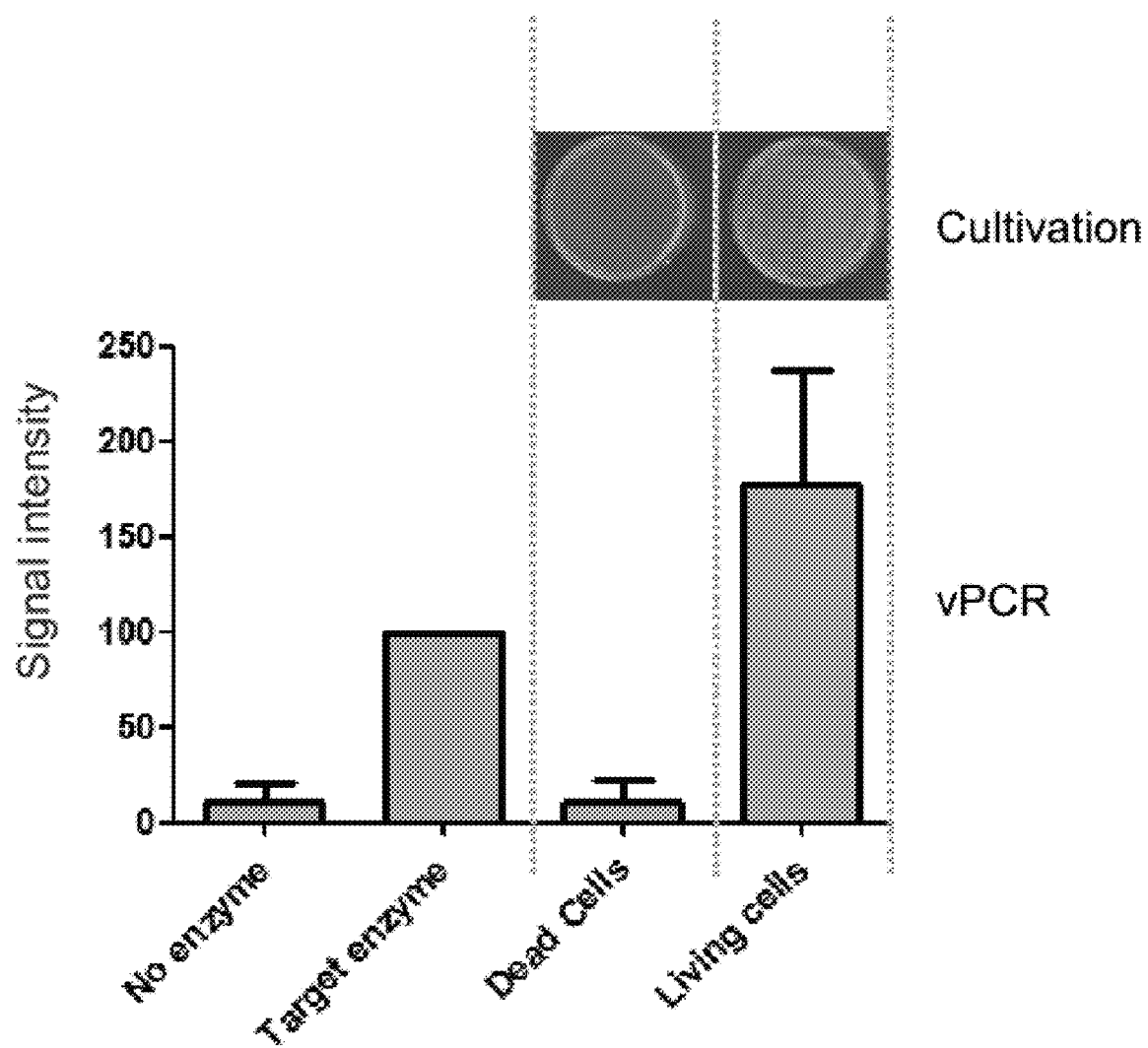
FIG. 5 shows that the method of the invention is able to discriminate between viable, untreated cells and cells killed by autoclavation.

To test if the technology can discriminate between living and dead bacteria, a portion of model target bacteria (EcoRI expressing E. coli, RY13) were split in two. One half was killed by autoclavation and the other half left untreated. Lysate of the two cell-portions were tested using the present technology.
Results The method of the invention was used for analysis of 4 sample types (EcoRI substrate set):
1) No enzyme or lysate added
2) purified EcoRI added
3) lysate from killed (autoclavation) RY13 cells added
4) lysate from untreated (living) RY13 cells added In addition, an aliquot of the two portions of cells (killed and untreated) was plated on an agar plate to verify that the treatment had worked (photos above graph in FIG. 5). Living cells grew as expected, whereas the killed cells did not (FIG. 5).
Conclusion The method of the invention can specifically detect only living bacteria.

Example 7—Detection of a Small Sample Containing a Model Bacteria Expressing EcoRI Using Microfluidics Aim of Example:

To fully exploit the potential of the isothermal nature of the technology and to move towards a simple, on-site methodology we tested if a small sample could be lysed using a simple handheld device based on a microfluidic chip. The sample is mixed with substrate (in this model case the substrate set for EcoRI), ligase, and lysozyme. This aqueous solution is mixed with oil (Pico Surf 1, 2% in Novec 7500) by vortexing. The vortexing creates small picoliter sized water in oil droplets that serve as reaction chambers for the core reaction (the endonuclease cleavage and the subsequent ligation). Lysis is achieved by the combination of lysozyme and the mechanical disruption by transfer through the serpentine channel in the microfluidic chip (see also FIGS. 7 and 8).

Results

Figure 6:
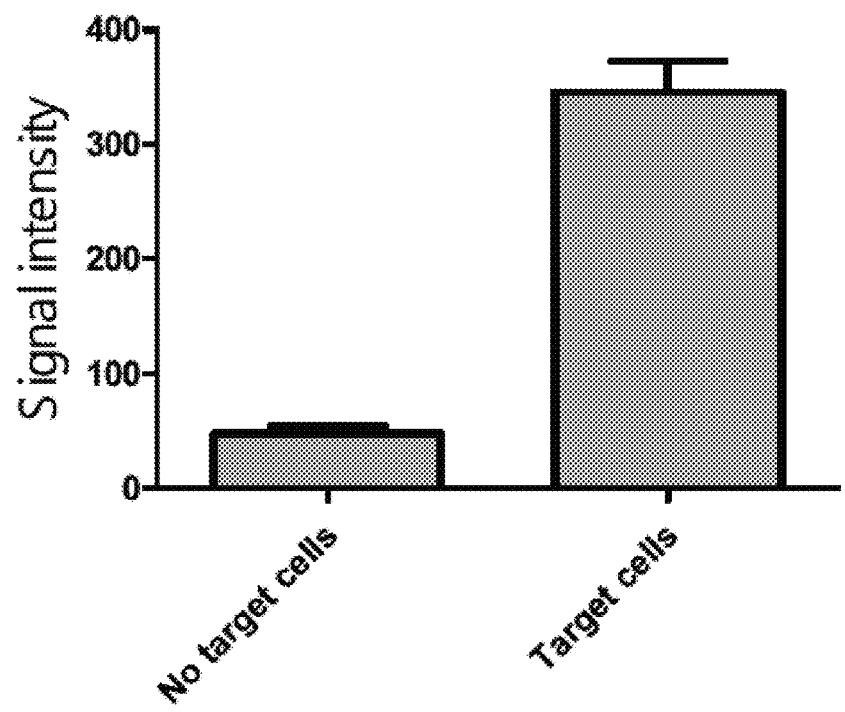
FIG. 6 shows detection of a small sample containing a model bacteria expressing EcoRI using microfluidics.

EcoRI expressing *E. coli* (RY13, target cells) were tested using the above described microfluidics strategy. A significant increase in the number of signals was observed upon inclusion of RY13 cells (FIG. 6).

Conclusion

The above results indicate that the entire core reaction may be performed in a simple one-step reaction and using only a small volume of sample. This represents an important step on the way towards development of a simple all-in-one device for bacterial detection. Further, it is shown that the steps b) and c) can be performed simultaneously.

Example 8—Identification of Endonucleases in Bacteria

Aim

To identify combinations of endonucleases which are considered specific for different types of bacteria.

The REBASE database (http://rebase.neb.com), was used to search for restriction endonucleases that the bacteria of interest—e.g. *Listeria monocytogenes*—is predicted to express. A set of three endonucleases was chosen and the REBASE database was then used to search for other organisms predicted to express an alike set of endonucleases. If an alike set of endonucleases was found in another organism, a new set of endonucleases from the bacteria of interest was tested. The final sets used will be verified using bioinformatics and genomic sequencing when needed.

Example 9—Detection of Target Enzyme EcoRI in Milk and Cream

Aim

To test if the method of the invention is able to discriminate between target bacteria and non-target bacteria in the presence of a food matrix.

Test: *E. coli* that either did not (strain: DH5α) or did express EcoRI (strain: RY13) were mixed with cream (FIG. 13A) or milk (FIG. 13B). The cells were lysed in the presence of the food item and the rest of the assay was performed as described in example 1.

Methods 20 mg of bacterial cell pellet was dissolved in 200 μL cream or milk. Lysis buffer was added to a final volume of 1 mL (final concentrations: 10 mM Tris-HCl (pH 7.5); 1 mM DTT; 19 mM NaF; 1 mM Beta Glycerophosphate (disodium salt); Roche proteases inhibitors cocktail, EDTA free (as described by supplier); 1 mM PMSF; and 20 v % of milk or cream when indicated). The mixture was incubated on ice and sonicated as described in example 1.

The following oligonucleotides were used:
REN2-ID33-EcoRI: Seq ID NO: 1
REN2-PB-EcoRI: Seq ID NO: 2
Primer: SEQ ID NO: 9
Detection probe: SEQ ID NO: 10

Results and Conclusions:

The results show that the method of the invention can discriminate between target and off-target bacteria in the presence of 20 v % cream or milk. The presence of the food matrix does not hamper the reaction significantly.

Example 10—Detection of XhoI in *Mycobacteria* with Optimized Primer

Aim of Example:

In order to increase the specificity of the assay, we designed a new primer (and probe) for rolling circle amplification (RCA). This primer anneals across the fusion site generated by fusion of the two substrate molecules. This means that RCA only occurs when the two hairpin substrates have been specifically digested and joined together. Since the primer have to anneal in a double-stranded region we added two 'locked nucleic acids' (LNA) in both the 5' and the 3' end of the primer, which enhances hybridization.

Method

The protocol described in example 1 was followed for the generation of circles. Two hairpin shaped DNA substrates containing specific restriction sites for XhoI were subjected to digestion with purified XhoI, extract from *Mycobacteria smegmatis* (expected to express XhoI) and extract from an *E. coli* bacterium called RY13 (expected not to express XhoI). Following digestion, the samples were ligated and then digested with exonucleases.

For this setup, the samples were then subjected to RCA with the abovementioned LNA primer labelled with a fluorophore. The LNA primer could hence also function as a detection probe and hybridized to the tandem repeats of the RCA product, enabling visualization in the fluorescence microscope without hybridization of other detection probes.

The following oligonucleotides were used:
REN2-ID33-XhoI: SEQ ID NO: 3
REN2B-PB-XhoI: SEQ ID NO: 18
Primer and detection probe: SEQ ID NO: 23

Results

With the method described above, we were able to demonstrate that the LNA primer can be used for detection of XhoI activity. The results can be seen in FIG. 14. The primer functioned as both a primer and a probe, removing a step in the protocol. The LNA primer assists in specific detection of XhoI as it generates signals with the samples digested with *M. smegmatis* (MS) extract and not with RY13 extract.

Conclusion:

The LNA primer specifically detects XhoI in *M. smegmatis* samples.

Example 11: Test of Substrates for MboI and BciVI Using Purified Endonucleases Aim of Example:

Bioinformatic analysis has pointed out MboI, Lmo911II, and BciVI or isoschizomers thereof as possible indicators of viable *Listeria*. We have initiated the test of substrates designed for MboI and BciVI using purified enzymes.

Materials and Methods:
  Substrates and probes:
    REN2-ID33-BciVI: SEQ ID NO: 13
    REN2-PB-BciVI: SEQ ID NO: 14
    REN2-ID33-MboI: SEQ ID NO: 15
    REN2-PB-MboI: SEQ ID NO: 16
    Primer: SEQ ID NO: 9
    Detection probe: SEQ ID NO: 10
  The experiments are performed with purified MboI and BciVI as described for other endonucleases in the section "Testing purified enzymes" of example 1.
Results
  Substrate sets carrying the MboI or the BciVI cleavage sites were tested using 2 units of pure endonuclease (columns marked "MboI sub.+MboI" and "BciVI sub+BciVI" in FIG. 15). The samples where purified endonucleases were omitted, gave significantly less signal than did the samples with purified endonuclease.
Conclusion
  The substrates designed for MboI and BciVI are recognized and processed by purified MboI and BciVI respectively, indicating that viable *Listeria* may be detected using the method of the invention.

Example 12—Elimination of Off-Target Effects with RY13 by Redesigning One of the Two Substrates Aim of Example
  The aim with this example is to remove off-target effects and increase the specificity of the assay when using bacterial extract. For this purpose, the stem region in one of the two hairpin DNA substrates was redesigned to avoid potential hybridization of the substrates following different activities in the bacterial extract such as cleavage with nucleases other than the target nuclease.
Method
  Using the protocol described in the materials and methods example (example 1), the redesigned substrates were tested (FIG. 16) with extract from *Mycobacteria smegmatis* (MS) and the *E. coli* bacterium RY13. According to database analyses MS expresses XhoI, while RY13 does not express XhoI.
  Substrates and probes:
    Pair 1 (re-designed with different stems)
    REN2-ID33-XhoI: SEQ ID NO: 3
    REN2B-PB-XhoI: SEQ ID NO: 18.
    Pair 2 (designed with identical stems)
    REN2-ID33-XhoI: SEQ ID NO: 3
    REN2-PB-XhoI: SEQ ID NO: 4
    Primer: SEQ ID NO: 9
    Detection probe: SEQ ID NO: 10
Conclusion
  Redesigning one of the two hairpin substrates, resulting in non-identical sequences in the stem region of the substrates, eliminates off-target effects of RY13 on XhoI specific substrates.

Example 13—Definition of *Listeria* Relevant Target Enzyme Sets

Aim of Example
  We identified 12 putative sets of enzymes for detection of *Listeria*. These sets consist of three enzymes each and comprise a total of eight restriction endonucleases of which six have commercially available isoshchizomers (BbvI, BciVI, HaeIII, MboI, SalI, TseI) and two are prototypes with known recognition sequence (BbvII, Lmo911II).
  The sets were derived based of a defined workflow procedure:
    a. Advanced search at REBASE database (http://rebase.neb.com) with criteria 'organism=*Listeria*'; 'Type II', 'Restriction enzyme', 'is neoschizomer=y;n' and retrieval of protein sequences.
    b. For sequences of restriction endonucleases occurring above a threshold (n=3) representative members were selected following multi-sequence alignment (MUSCLE and Clustal Omega at https://www.ebi.ac.uk/Tools/msa/). To assess potential hits of the selected representative sequences to other bacteria Microbial Protein BLAST (https://blast.ncbi.nlm.nih.gov) was performed against non-redundant RefSeq proteins (e-value cut-off 0.001) and significant hits, linage- and taxonomy reports were inspected.
    c. Criteria for enzymes were defined based on species specificity, validation status (i.e. non putative) and frequency in the downloaded REBASE sequences. Enzymes were ranked and combined into sets which were evaluated with regard to the BLAST results.
Results
  Eight putative sets of enzymes for detection of *Listeria monocytogenes* (Limo)
    # Limo-set1: Lmo911, BciVI, MboI
    # Limo-set2: Lmo911, BciVI, SalI
    # Limo-set3: Lmo911, BciVI, TseI
    # Limo-set4: Lmo911, BciVI, HaeIII
    # Limo-set5: Lmo911, BciVI, BbvII
    # Limo-set5: Lmo911, MboI, SalI
    # Limo-set6: Lmo911, MboI, TseI
    # Limo-set7: Lmo911, MboI, HaeIII
    # Limo-set8: Lmo911, MboI, BbvII
  Two putative sets of enzymes for detection of *Listeria* sp. (Lisp)
    # Lisp-set1: Lmo911, BciVI, BbvI
    # Lisp-set2: Lmo911, MboI, BbvI
Conclusion
  The workflow provides a structured procedure for selection of candidate enzymes and their evaluation against known bacterial proteins and as well as comparison and ranking of the putative target sets.

Example 14—Titration of RY13 Bacteria (E, Coil) and *Mycobacteria smegmatis* Amounts Aim of Example
  The aim of this example was to investigate the detection limit of the protocol of the invention. In order to do this, titrations of RY13 bacteria (*E. coli*) and *Mycobacteria smegmatis* extracts were made.
Method
  RY13 bacteria:
    The protocol described in example 1 was followed with 80 to 0 μg of RY13 bacteria extract.
    The following oligonucleotides were used:
    REN2-ID33-EcoRI: SEQ ID NO: 1
    REN2B-PB-EcoRI: SEQ ID NO: 17
    Primer: SEQ ID NO: 9
    Detection probe: SEQ ID NO: 10
  *Mycobacteria smegmatis*:
    The protocol described in example 1 was followed with *M. smegmatis* extracts with 160.000 to 25 colony forming units (CFU). The detection limit was also found for the protocol modified with the LNA primer (also used for FIG.

14). In this setup the normal protocol was followed for the generation of DNA circles from the two hairpin DNA substrates. After circle generation, RCA was performed using the previous mentioned LNA primer. This LNA primer was modified with a fluorophore, hence also functioned as a detection probe.

The following oligonucleotides were used:
REN2-ID33-XhoI: SEQ ID NO: 3
REN2B-PB-XhoI: SEQ ID NO: 18
Detection probe: SEQ ID NO: 23 (see FIG. 17C) or SEQ ID NO: 10 (see FIG. 17B)
Primer: SEQ ID NO: 9

Results

RY13 bacteria (*E. coli*):

The signal intensity obtained with the different bacteria amounts is depicted in FIG. 17A.

*Mycobacteria smegmatis:*

Signal intensity obtained with *M. smegmatis* extract with decreasing CFU. The results from the protocol similar to the one described in example 1 is depicted in FIG. 17B, while the protocol modified with the LNA primer can be seen in FIG. 17C.

Conclusion

The protocol was able to detect 0.4 µg RY13 bacteria. The bacteria extract was not diluted enough to find the actual detection limit.

For *M. smegmatis* a detection level down to 25 or 50 CFU were obtained when using the LNA primer.

Example 15—One Step Procedure

Aim of Example

The aim of this experiment was to test if all reagents could be mixed and all sub-reactions run in a single incubation step.

Materials and Methods

The aim of this experiment was to test if all reagents could be mixed and all sub-reactions run in a single incubation step.

*E. coli* cells (Off target: DH5-alpha or Target: RY13), were resuspended in lysis buffer (1 mL per 20 mg cell pellet). Lysis buffer: 10 mM Tris-HCL pH 7.5; 1 mM DTT; 0.1 V % PMSF; 19 mM NaF; 1 mM Beta Glycerophosphate; Roche protease inhibitor cocktail, EDTA free, 50 µg/mL lysozyme. Keep on ice for 30 minutes. Mix:

| Component | Final concentrations |
| --- | --- |
| Lysis mix (cells, lysozyme, lysisbuffer) | 75 V % |
| DNA substrate 1 (SEQ ID NO: 1) | 0.9 pmol/µL |
| DNA substrate 2 (SEQ ID NO: 2) | 0.9 pmol/µL |
| Detection probe 3 (SEQ ID NO: 12) | 0.9 pmol/µL |
| RCA primer SEQ ID NO: 9) | 4.5 pmol/µL |
| CutSmart buffer (NEB) | 1× |
| T4 DNA Ligase (Invitrogen) | 1 U/56 µL |
| Phi29 (ThermoFisher) | 0.9 U/µL |
| ATP | 10 mM |
| dNTP's | 1 mM |

The mixture was mixed with 2 volumes of oil (2% PicoSurf 1 in FC40) and vortexed for 1 minute. The emulsion was then pushed through a microfluidic chip with one inlet and one outlet separated by a serpentine channel (see also FIGS. 7 and 8). After 2 hours, droplets were analyzed using a fluorescence microscope Results As shown in FIG. 18, a much higher signal was obtained from the sample comprising the targets cells compared to the sample without cells and the sample with off-target cells.

Conclusion

The data presented show that it is possible to mix all the components in a single mixture, and still receive positive results.

---

The invention claimed is:

1. A method for screening for Type II restriction endonuclease activity in a sample, the method comprising:
   a) adding to a provided sample to be analyzed at least one first oligonucleotide, to obtain a first reaction composition, the at least one first oligonucleotide comprising a hairpin structure, wherein the stem of said hairpin structure comprises a first cleavage site for a first Type II restriction endonuclease;
   b) adding a ligase to the first reaction composition obtained in a), to circularize at least two of the first oligonucleotides if a Type II restriction endonuclease present in the sample has cleaved the cleavage site in the first oligonucleotide, wherein the produced circularized molecules comprise part of stem-loop structures of the first oligonucleotide after Type II restriction endonuclease cleavage;
   c performing an amplification reaction using the at least first circularized oligonucleotides as template; and
   d detecting the amplified product from step c), thereby determining Type II restriction endonuclease activity in said sample.

2. The method according to claim 1, wherein the sample is a biological sample.

3. The method according to claim 1, wherein the sample is a biological sample, selected from the group consisting of tissue samples, saliva, blood, food samples, surface swipes, environmental samples, and plant samples.

4. The method according to claim 1, wherein the sample is a biological sample selected from the group consisting of animal feed or food for human consumption, dairy products, milk, cream, fermented milk products, cheeses, butter, plants, vegetables, fruit, fish, fish products, egg, egg products, condiments and spices.

5. The method according to claim 1, wherein the presence of Type II restriction endonuclease activity is indicative of viable microorganisms.

6. The method according to claim 1, wherein the presence of Type II restriction endonuclease activity is indicative of viable bacteria.

7. The method according to claim 1, wherein the presence of Type II restriction endonuclease activity is indicative of viable bacteria selected from the group consisting of *listeria*,

*Pseudomonas, Salmonella, Campylobacter, E.coli, Staphylococci, MRSA, Mycobacteria, Streptococcus, Neisseria, Klepsiella,* and *Vibrio*.

8. The method according to claim 1, wherein at least one further second oligonucleotide is added to the sample in step a), wherein said second oligonucleotide comprises a hairpin structure, wherein the stem of said hairpin structure comprises a cleavage site for said first Type II restriction endonuclease.

9. The method according to claim 1, wherein the first restriction site for a first Type II restriction endonuclease is selected from the group consisting of restriction sites specific for EcoRI, PstI, XhoI, SacII, MboI, Lmo911II, BciVI, HaeIII, NlaIII, HphI, AvaII, PvuII, XmaIII, Fnu4HI, ScrFI, MtuHN878II or SmlI, and isoschizomers thereof.

10. The method according to claim 1, further comprising screening said sample for Type II restriction endonuclease activity of at least one further Type II restriction endonuclease, using one or more further oligonucleotides comprising a hairpin structure, wherein the stem of said hairpin structure comprises a second cleavage site for a second Type II restriction endonuclease.

11. The method according to claim 1, wherein said oligonucleotides have a length in the range 30-120 nucleotides.

12. The method according to claim 1, wherein the first oligonucleotide is blocked at the 5'-end and/or the 3'-end to minimize undesired ligation reactions and/or exonuclease activity on the nucleotides.

13. The method according to claim 1, wherein step a) and step b) are performed simultaneously, so that said ligase is added to the sample together with the at least first oligonucleotide.

14. The method according to claim 1, wherein step a), step b) and step c) are performed simultaneously, so that said circularization, ligation and amplification is performed simultaneously.

15. The method according to claim 1, wherein said amplification reaction d) is performed by a method selected from the group consisting of Rolling Circle Amplification (RCA), PCR, real-time-PCR, Southern blotting, quantitative PCR (qPCR), restriction fragment length dimorphism-PCR (RFLD-PCR), primer extension, DNA array technology, LAMP and isothermal amplification.

16. The method according to claim 1, wherein said amplification reaction d) is performed by Rolling Circle Amplification (RCA).

17. The method according to claim 1, wherein detection of Type II restriction endonuclease activity of:
XhoI, PstI and/or SacII or isoschizomers thereof is indicative of viable *Pseudomanas* in said sample;
MboI, Lmo911II and/or BciVI or isoschizomers thereof is indicative of viable *Listeria* in said sample;
HaeIII, NlaIII, and/or HphI or isoschizomers thereof is indicative of viable *Campylobacter* in said sample;
AvaII, PvuII and/or XmaIII or isoschizomers thereof is indicative of viable *Salmonella* in said sample;
Fnu4HI, ScrFI, and/or SmlI or isoschizomers thereof is indicative of viable *Staphylococcus* in said sample;
MtuHN878II is indicative of viable mycobacteria belonging to the *Mycobacterium tuberculosis* complex in said sample.

18. The method according to claim 1, wherein the detection of endonuclease activity of:
Lmo911, BciVI, and/or BbvI or isoschizomers thereof; or
Lmo911, MboI, and/or BbvI or isoschizomers thereof;
is indicative of viable *Listeria* sp..

19. The method according to claim 1, wherein the detection of endonuclease activity of:
Lmo911, BciVI, and/or MboI or isoschizomers thereof;
Lmo911, BciVI, and/or SalI or isoschizomers thereof;
Lmo911, BciVI, and/or TseI or isoschizomers thereof;
Lmo911, BciVI, and/or HaeIII or isoschizomers thereof;
Lmo911, BciVI, and/or BbvII or isoschizomers thereof;
Lmo911, MboI, and/or SalI or isoschizomers thereof;
Lmo911, MboI, and/or TseI or isoschizomers thereof;
Lmo911, MboI, and/or HaeIII or isoschizomers thereof; or
Lmo911, MboI, and/or BbvII or isoschizomers thereof;
is indicative of viable *Listeria*.

20. The method according to claim 1, wherein at least one further second oligonucleotide is added to the sample in step a), wherein said second oligonucleotide comprises a hairpin structure, wherein the stem of said hairpin structure comprises a cleavage site for said first Type II restriction endonuclease;
wherein the first oligonucleotide and the second oligonucleotide are different in sequence;
wherein said first oligonucleotide and said second oligonucleotide have different loop sequences; and
wherein said first oligonucleotide and said second oligonucleotide have different stem sequences.

21. A method for screening for Type II restriction endonuclease activity in a sample, the method comprising:
a) adding to a provided sample to be analyzed at least one first oligonucleotide, to obtain a first reaction composition, the at least one first oligonucleotide comprising a hairpin structure, wherein the stem of said hairpin structure comprises a first cleavage site for a first Type II restriction endonuclease;
b) adding a ligase and a support oligonucleotide to the first reaction composition obtained in a), the support oligonucleotide facilitating hybridization by bridging the 5'-end and the 3'-end of said first oligonucleotide after endonuclease cleavage, to circularize the first oligonucleotides if a Type II restriction endonuclease present in the sample has cleaved the cleavage site in the first oligonucleotide, wherein the produced circularized molecules comprise part of the stem-loop structures of the first oligonucleotides after Type II restriction endonuclease cleavage;
c) performing an amplification reaction using the at least first circularized oligonucleotides as template; and
d) detecting the amplified product from step c), thereby determining Type II restriction endonuclease activity in said sample.

22. A method for screening for Type II restriction endonuclease activity in a sample, the method comprising:
a) adding to a provided sample to be analyzed at least one first oligonucleotide and at least one second oligonucleotide, to obtain a first reaction composition, the at least one first oligonucleotide and the at least one second oligonucleotide comprising a hairpin structure, wherein the stem of said hairpin structure comprises a first cleavage site for a first Type II restriction endonuclease;
b) adding a ligase to the first reaction composition obtained in a), to circularize the at least first oligonucleotide and the at least one second oligonucleotide if a Type II restriction endonuclease present in the sample has cleaved the cleavage site in the first oligonucleotide, wherein the produced circularized molecules comprise part of stem-loop structures of the first oligonucleotide and part of stem-loop structures of the second oligonucleotide after Type II restriction endonuclease cleavage;

c) performing an amplification reaction using the circularized oligonucleotides as template; and d) detecting the amplified product from step c), thereby determining Type II restriction endonuclease activity in said sample, wherein the first oligonucleotide and the second oligonucleotide are different in sequence.

23. The method according to claim 22, wherein said first oligonucleotide and said second oligonucleotide have different loop sequences or different stem sequences.

* * * * *

SEQUENCE LISTING

<160> NUMBER OF SEQ ID NOS: 24

<210> SEQ ID NO 1
<211> LENGTH: 101
<212> TYPE: DNA
<213> ORGANISM: Artificial Sequence
<220> FEATURE:
<223> OTHER INFORMATION: Synthetic
<220> FEATURE:
<221> NAME/KEY: Amine
<222> LOCATION: (1)..(1)
<220> FEATURE:
<221> NAME/KEY: Amine
<222> LOCATION: (101)..(101)

<400> SEQUENCE: 1
atttgacgaa ttcgtcgtat aggaacttcg aacgactcgc ctcaatgcac atgtttggct      60
cccgagtcgt tcgaagttcc tatacgacga attcgtcaaa t      101

<210> SEQ ID NO 2
<211> LENGTH: 96
<212> TYPE: DNA
<213> ORGANISM: Artificial Sequence
<220> FEATURE:
<223> OTHER INFORMATION: Synthetic
<220> FEATURE:
<221> NAME/KEY: Amine
<222> LOCATION: (1)..(1)
<220> FEATURE:

```
<221> NAME/KEY: Amine
<222> LOCATION: (96)..(96)

<400> SEQUENCE: 2
atttccagaa ttctgggtat aggaacttcg aacgactcga ctgtgaagat cgcttatcga    60
gtcgttcgaa gttcctatac ccagaattct ggaaat                              96

<210> SEQ ID NO 3
<211> LENGTH: 101
<212> TYPE: DNA
<213> ORGANISM: Artificial Sequence
<220> FEATURE:
<223> OTHER INFORMATION: Synthtetic
<220> FEATURE:
<221> NAME/KEY: Amine
<222> LOCATION: (1)..(1)
<220> FEATURE:
<221> NAME/KEY: Amine
<222> LOCATION: (101)..(101)

<400> SEQUENCE: 3
atttgacctc gaggtcgtat aggaacttcg aacgactcgc tcaatgcac atgtttggct     60 cccgagtcgt tcgaagttcc tatacgacct cgaggtcaaa t                       101

<210> SEQ ID NO 4
<211> LENGTH: 96
<212> TYPE: DNA
<213> ORGANISM: Artificial Sequence
<220> FEATURE:
<223> OTHER INFORMATION: Synthetic
<220> FEATURE:
<221> NAME/KEY: Amine
<222> LOCATION: (1)..(1)
<220> FEATURE:
<221> NAME/KEY: Amine
<222> LOCATION: (96)..(96)

<400> SEQUENCE: 4
atttccactc gagtgggtat aggaacttcg aacgactcga ctgtgaagat cgcttatcga    60
gtcgttcgaa gttcctatac ccactcgagt ggaaat                              96

<210> SEQ ID NO 5
<211> LENGTH: 101
<212> TYPE: DNA
<213> ORGANISM: Artificial Sequence
<220> FEATURE:
<223> OTHER INFORMATION: Synthetic
<220> FEATURE:
<221> NAME/KEY: Amine
<222> LOCATION: (1)..(1)
<220> FEATURE:
<221> NAME/KEY: Amine
<222> LOCATION: (101)..(101)

<400> SEQUENCE: 5
atttgacccg cgggtcgtat aggaacttcg aacgactcgc tcaatgcac atgtttggct     60 cccgagtcgt tcgaagttcc tatacgaccc gcgggtcaaa t                       101

<210> SEQ ID NO 6
<211> LENGTH: 96
<212> TYPE: DNA
<213> ORGANISM: Artificial Sequence
<220> FEATURE:
<223> OTHER INFORMATION: Synthetic
<220> FEATURE:
<221> NAME/KEY: Amine
<222> LOCATION: (1)..(1)
```

```
<220> FEATURE:
<221> NAME/KEY: Amine
<222> LOCATION: (96)..(96)

<400> SEQUENCE: 6
atttccaccg cggtgggtat aggaacttcg aacgactcga ctgtgaagat cgcttatcga    60
gtcgttcgaa gttcctatac ccaccgcggt ggaaat                              96

<210> SEQ ID NO 7
<211> LENGTH: 101
<212> TYPE: DNA
<213> ORGANISM: Artificial Sequence
<220> FEATURE:
<223> OTHER INFORMATION: Synthetic
<220> FEATURE:
<221> NAME/KEY: Amine
<222> LOCATION: (1)..(1)
<220> FEATURE:
<221> NAME/KEY: Amine
<222> LOCATION: (101)..(101)

<400> SEQUENCE: 7
atttgacctg caggtcgtat aggaacttcg aacgactcgc tcaatgcac atgtttggct     60 cccgagtcgt tcgaagttcc tatacgacct gcaggtcaaa t                       101

<210> SEQ ID NO 8
<211> LENGTH: 96
<212> TYPE: DNA
<213> ORGANISM: Artificial Sequence
<220> FEATURE:
<223> OTHER INFORMATION: Synthetic
<220> FEATURE:
<221> NAME/KEY: Amine
<222> LOCATION: (1)..(1)
<220> FEATURE:
<221> NAME/KEY: Amine
<222> LOCATION: (96)..(96)

<400> SEQUENCE: 8
atttccactg cagtgggtat aggaacttcg aacgactcga ctgtgaagat cgcttatcga    60
gtcgttcgaa gttcctatac ccactgcagt ggaaat                              96

<210> SEQ ID NO 9
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: Amine
<222> LOCATION: (1)..(1)

<400> SEQUENCE: 9
ccaaccaacc aaccaaataa gcgatcttca cagt                                34

<210> SEQ ID NO 10
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: FAM
<222> LOCATION: (1)..(1)

<400> SEQUENCE: 10
cctcaatgca catgtttggc tcc                                            23
```

<210> SEQ ID NO 11
<211> LENGTH: 28
<212> TYPE: RNA
<213> ORGANISM: Artificial Sequence
<220> FEATURE:
<223> OTHER INFORMATION: Detection probe 2
<220> FEATURE:
<221> NAME/KEY: CAL Fluor 590
<222> LOCATION: (1)..(1)
<220> FEATURE:
<221> NAME/KEY: misc_feature
<222> LOCATION: (1)..(28)
<223> OTHER INFORMATION: 2'OMe-RNA sequence
<220> FEATURE:
<221> NAME/KEY: BHQ-2 (Black Hole Quencher-2)
<222> LOCATION: (28)..(28)
<223> OTHER INFORMATION: 2'OMe-RNA sequence

<400> SEQUENCE: 11
guagaccuca augcugcugc uguacuac                                      28

<210> SEQ ID NO 12
<211> LENGTH: 25
<212> TYPE: RNA
<213> ORGANISM: Artificial Sequence
<220> FEATURE:
<223> OTHER INFORMATION: Detection probe 3
<220> FEATURE:
<221> NAME/KEY: FAM
<222> LOCATION: (1)..(1)
<220> FEATURE:
<221> NAME/KEY: misc_feature
<222> LOCATION: (1)..(25)
<223> OTHER INFORMATION: 2'OMe-RNA sequence
<220> FEATURE:
<221> NAME/KEY: Black Hole Quencher-1
<222> LOCATION: (25)..(25)

<400> SEQUENCE: 12
agccaccuca augcacaugu uuggu                                         25

<210> SEQ ID NO 13
<211> LENGTH: 99
<212> TYPE: DNA
<213> ORGANISM: Artificial Sequence
<220> FEATURE:
<223> OTHER INFORMATION: probe
<220> FEATURE:
<221> NAME/KEY: Amine
<222> LOCATION: (1)..(1)
<220> FEATURE:
<221> NAME/KEY: Amine
<222> LOCATION: (99)..(99)

<400> SEQUENCE: 13
atttgacgta tccaaatttg tcgacttcga acgactcgcc tcaatgcaca tgtttggctc    60
ccgagtcgtt cgaagtcgac aaatttggat acgtcaaat                           99

<210> SEQ ID NO 14
<211> LENGTH: 94
<212> TYPE: DNA
<213> ORGANISM: Artificial Sequence
<220> FEATURE:
<223> OTHER INFORMATION: Probe
<220> FEATURE:
<221> NAME/KEY: Amine
<222> LOCATION: (1)..(1)
<220> FEATURE:
<221> NAME/KEY: Amine
<222> LOCATION: (94)..(94)

```
<400> SEQUENCE: 14
atttccagta tcctttaaat gggacttcga acgactcgac tgtgaagatc gcttatcgag      60
tcgttcgaag tcccatttaa aggatactgg aaat                                  94

<210> SEQ ID NO 15
<211> LENGTH: 97
<212> TYPE: DNA
<213> ORGANISM: Artificial Sequence
<220> FEATURE:
<223> OTHER INFORMATION: Probe
<220> FEATURE:
<221> NAME/KEY: Amine
<222> LOCATION: (1)..(1)
<220> FEATURE:
<221> NAME/KEY: Amine
<222> LOCATION: (97)..(97)

<400> SEQUENCE: 15
atttgacgat cgtcgtatag gaacttcgaa cgactcgcct caatgcacat gtttggctcc      60
cgagtcgttc gaagttccta tacgacgatc gtcaaat                               97

<210> SEQ ID NO 16
<211> LENGTH: 92
<212> TYPE: DNA
<213> ORGANISM: Artificial Sequence
<220> FEATURE:
<223> OTHER INFORMATION: Probe
<220> FEATURE:
<221> NAME/KEY: Amine
<222> LOCATION: (1)..(1)
<220> FEATURE:
<221> NAME/KEY: Amine
<222> LOCATION: (92)..(92)

<400> SEQUENCE: 16
atttccagat ctgggtatag gaacttcgaa cgactcgact gtgaagatcg cttatcgagt      60
cgttcgaagt tcctataccc agatctggaa at                                    92

<210> SEQ ID NO 17
<211> LENGTH: 96
<212> TYPE: DNA
<213> ORGANISM: Artificial Sequence
<220> FEATURE:
<223> OTHER INFORMATION: Probe
<220> FEATURE:
<221> NAME/KEY: Amine
<222> LOCATION: (1)..(1)
<220> FEATURE:
<221> NAME/KEY: Amine
<222> LOCATION: (96)..(96)

<400> SEQUENCE: 17
attcactgaa ttcagcgctt aggagtgcat atacgatgca ctgtgaagat cgcttatgca      60
tcgtatatgc actcctaagc gctgaattca gtgaat                                96

<210> SEQ ID NO 18
<211> LENGTH: 96
<212> TYPE: DNA
<213> ORGANISM: Artificial Sequence
<220> FEATURE:
<223> OTHER INFORMATION: Probe
<220> FEATURE:
<221> NAME/KEY: Amine
<222> LOCATION: (1)..(1)
<220> FEATURE:
<221> NAME/KEY: Amine
```

```
<222> LOCATION: (96)..(96)

<400> SEQUENCE: 18
attcactctc gagagcgctt aggagtgcat atacgatgca ctgtgaagat cgcttatgca      60
tcgtatatgc actcctaagc gctctcgaga gtgaat                               96

<210> SEQ ID NO 19
<211> LENGTH: 92
<212> TYPE: DNA
<213> ORGANISM: Artificial Sequence
<220> FEATURE:
<223> OTHER INFORMATION: Probe
<220> FEATURE:
<221> NAME/KEY: Amine
<222> LOCATION: (1)..(1)
<220> FEATURE:
<221> NAME/KEY: Amine
<222> LOCATION: (92)..(92)

<400> SEQUENCE: 19
attcactgat cagcgcttag gagtgcatat acgatgcact gtgaagatcg cttatgcatc      60
gtatatgcac tcctaagcgc tgatcagtga at                                   92

<210> SEQ ID NO 20
<211> LENGTH: 118
<212> TYPE: DNA
<213> ORGANISM: Artificial Sequence
<220> FEATURE:
<223> OTHER INFORMATION: Probe
<220> FEATURE:
<221> NAME/KEY: Amine
<222> LOCATION: (1)..(1)
<220> FEATURE:
<221> NAME/KEY: Amine
<222> LOCATION: (118)..(118)

<400> SEQUENCE: 20
attcactcat cagtgatcta aagagcgct taggagtgca tatacgatgc actgtgaaga      60
tcgcttatgc atcgtatatg cactcctaag cgctcttcta gatcactgat gagtgaat      118

<210> SEQ ID NO 21
<211> LENGTH: 94
<212> TYPE: DNA
<213> ORGANISM: Artificial Sequence
<220> FEATURE:
<223> OTHER INFORMATION: Probe
<220> FEATURE:
<221> NAME/KEY: Amine
<222> LOCATION: (1)..(1)
<220> FEATURE:
<221> NAME/KEY: Amine
<222> LOCATION: (94)..(94)

<400> SEQUENCE: 21
attcactgta tcctttaaaa gcgctgtgca tacgatgcac tgtgaagatc gcttatgcat      60
cgtatgcaca gcgcttttaa aggatacagt gaat                                 94

<210> SEQ ID NO 22
<211> LENGTH: 119
<212> TYPE: DNA
<213> ORGANISM: Artificial Sequence
<220> FEATURE:
<223> OTHER INFORMATION: Probe
<220> FEATURE:
<221> NAME/KEY: Amine
<222> LOCATION: (1)..(1)
<220> FEATURE:
```

```
<221> NAME/KEY: Amine
<222> LOCATION: (119)..(119)

<400> SEQUENCE: 22
atttgacggt cacgagtaga aggtcgtata ggaacttcga acgactcgcc tcaatgcaca      60
tgtttggctc ccgagtcgtt cgaagttcct atacgacctt ctactcgtga ccgtcaaat     119

<210> SEQ ID NO 23
<211> LENGTH: 10
<212> TYPE: DNA
<213> ORGANISM: Artificial Sequence
<220> FEATURE:
<223> OTHER INFORMATION: Primer/detection probe
<220> FEATURE:
<221> NAME/KEY: LNA
<222> LOCATION: (1)..(2)
<220> FEATURE:
<221> NAME/KEY: TYE665
<222> LOCATION: (1)..(1)
<220> FEATURE:
<221> NAME/KEY: LNA
<222> LOCATION: (9)..(10)

<400> SEQUENCE: 23
tacgacctcg                                                            10

<210> SEQ ID NO 24
<211> LENGTH: 10
<212> TYPE: DNA
<213> ORGANISM: Artificial Sequence
<220> FEATURE:
<223> OTHER INFORMATION: Primer/detection probe
<220> FEATURE:
<221> NAME/KEY: LNA
<222> LOCATION: (1)..(2)
<220> FEATURE:
<221> NAME/KEY: FAM
<222> LOCATION: (1)..(1)
<220> FEATURE:
<221> NAME/KEY: LNA
<222> LOCATION: (9)..(10)

<400> SEQUENCE: 24
ctgaattcgt                                                            10
```